(12) United States Patent
Bobe et al.

(10) Patent No.: US 8,519,051 B2
(45) Date of Patent: Aug. 27, 2013

(54) BLOCK COPOLYMER FOR DRUG CONJUGATES AND PHARMACEUTICAL COMPOSITION

(75) Inventors: Iulian Bobe, Kashiwa (JP); Naoya Shibata, Kashiwa (JP); Hiroyuki Saito, Kashiwa (JP); Mitsunori Harada, Kashiwa (JP)

(73) Assignee: Nanocarrier Co., Ltd., Kashiwa-shi (JP)

( * ) Notice: Subject to any disclaimer, the term of this patent is extended or adjusted under 35 U.S.C. 154(b) by 468 days.

(21) Appl. No.: 12/445,710

(22) PCT Filed: Oct. 19, 2007

(86) PCT No.: PCT/JP2007/070865
§ 371 (c)(1),
(2), (4) Date: Apr. 15, 2009

(87) PCT Pub. No.: WO2008/047948
PCT Pub. Date: Apr. 24, 2008

(65) Prior Publication Data
US 2010/0298495 A1 Nov. 25, 2010

(30) Foreign Application Priority Data
Oct. 19, 2006 (JP) ................................ 2006-285469

(51) Int. Cl.
*C08L 89/00* (2006.01)
(52) U.S. Cl.
USPC ........ 525/54.11; 525/54.1; 424/497; 424/451
(58) Field of Classification Search
USPC ...................... 525/54.1, 54.11; 424/497, 451
See application file for complete search history.

(56) References Cited

U.S. PATENT DOCUMENTS

| 6,080,396 A | 6/2000 | Yokoyama et al. |
| 2001/0014354 A1 | 8/2001 | Yokoyama et al. |

FOREIGN PATENT DOCUMENTS

| EP | 1 127 570 A2 | 8/2001 |
| JP | 7-69900 A | 3/1995 |
| JP | 11335267 A | * 12/1999 |
| JP | 2001-226294 | 8/2001 |
| JP | 3270592 A | 4/2002 |
| JP | 2003-34653 A | 2/2003 |
| JP | 2004-18494 | 1/2004 |
| WO | WO 97/12895 | 4/1997 |
| WO | WO 2005-054302 | 6/2005 |
| WO | WO 2006/115293 | 11/2006 |

OTHER PUBLICATIONS

Bae et al. Angew. Chem. Int. Ed. 2003, 42, 4640-4643.*
Machine translation of JP 11335267 A (2011).*
Machine translation of WO 2006/115293 (2011).*
Younsoo Bae et al., "Multifunctional polymeric micelles with folate-mediated cancer cell targeting and pH-triggered drug releasing properties for active intracellular drug delivery," Molecular Biosystems, Sep. 2005, vol. 1, No. 3, pp. 242-250.
K. Ulbrich et al., "Polymeric anticancer drugs with pH-controlled activation," International Journal of Pharmaceutics, Jun. 11, 2004, vol. 277, No. 11, pp. 63-72.
G. Kwon et al., Block copolymer micelles for drug delivery: loading and release of doxorubicin, Journal of Controlled Release, Oct. 13, 1997, vol. 48, No. 2-3, pp. 195-201.
H. Dalton King et al., "Monoclonal Antibody Conjugates of Doxorubicin Prepared with Branched Peptide Linkers: Inhibition of Aggregation by Methoxytriethyleneglycol Chains" J. Med. Chem. 2002, 45, 4336-4343.
Karel Ulbrich et al., "Polymeric Anticancer Drugs with pH-controlled Activation," Advanced Drug Delivery Reviews 56 (2004) 1023-1050.
Roberta Cazzola et al., "pH sensitivity and plasma stability of Liposomes containing N-stearoylcysteamine," Biochimica et Biophysica Acta 1329 (1997) 291-301.
K. Ulbrich et al., "HPMA copolymers with pH-controlled release of doxorubicin In vitro cytotoxicity and in vivo antitumor activity," Journal of Controlled Release 87 (2003) 33-47.
Younsoo Bae et al., "Preparation and Biological Characterization of Polymeric Micelle Drug Carriers with Intracellular pH-Triggered Drug Release Property: Tumor Permeability, Controlled Subcellular Drug Distribution, and Enhanced in Vivo Antitumor Efficacy," Bioconjugate Chem. 2005, 16, 122-130.

* cited by examiner

*Primary Examiner* — Mark Kaucher
(74) *Attorney, Agent, or Firm* — Finnegan, Henderson, Farabow, Garrett & Dunner, L.L.P.

(57) ABSTRACT

The present invention provides a block copolymer for a drug conjugate which comprises a water-soluble polymer region consisting of polyethylene glycol and a polyamino acid region having a hydrazide group and a hydrophobic group in the side chain.

6 Claims, 6 Drawing Sheets

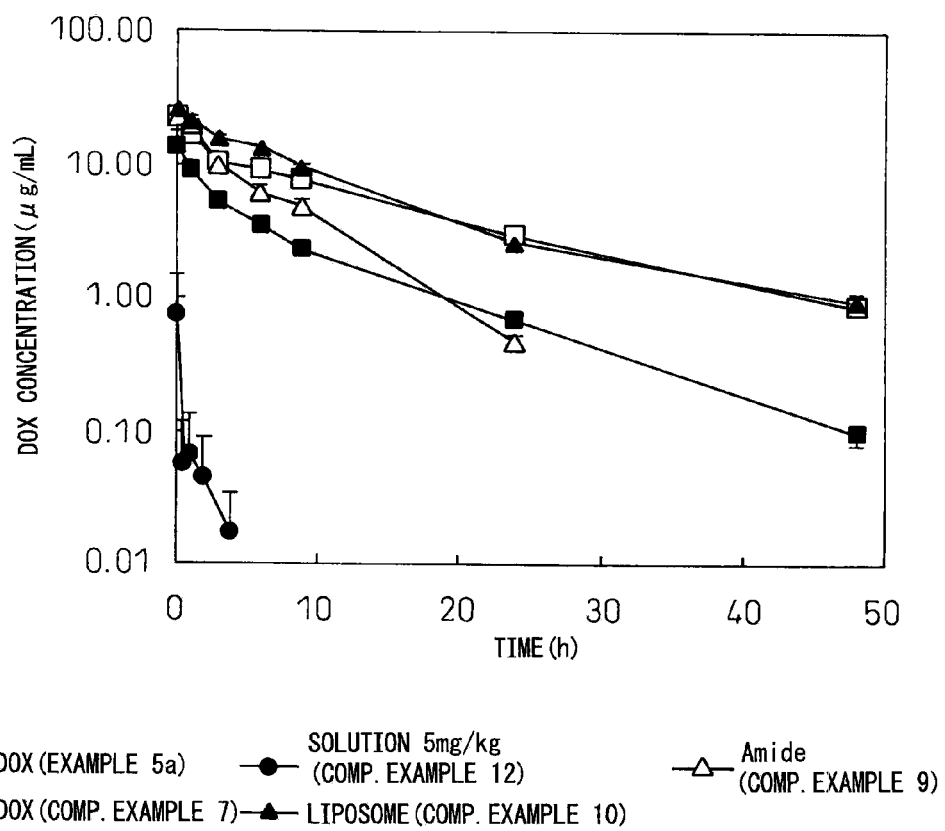

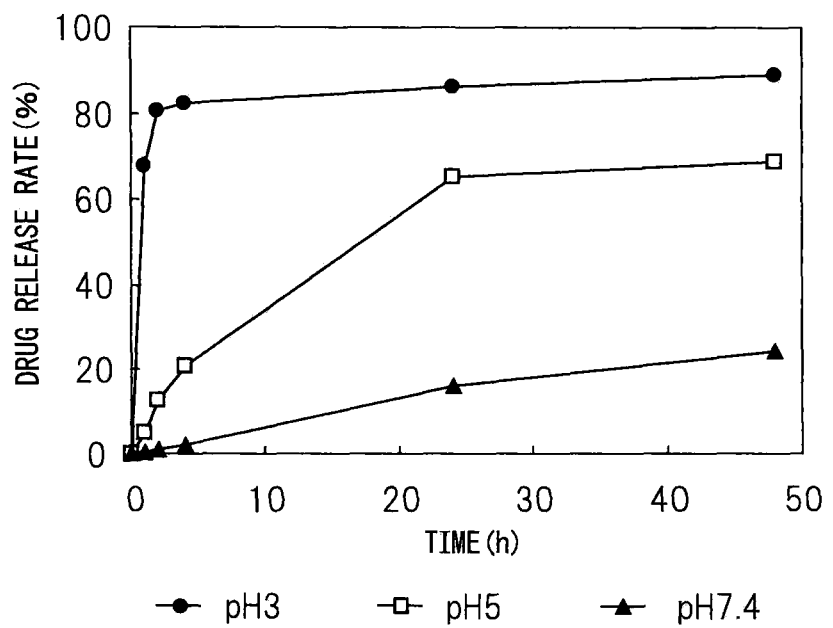

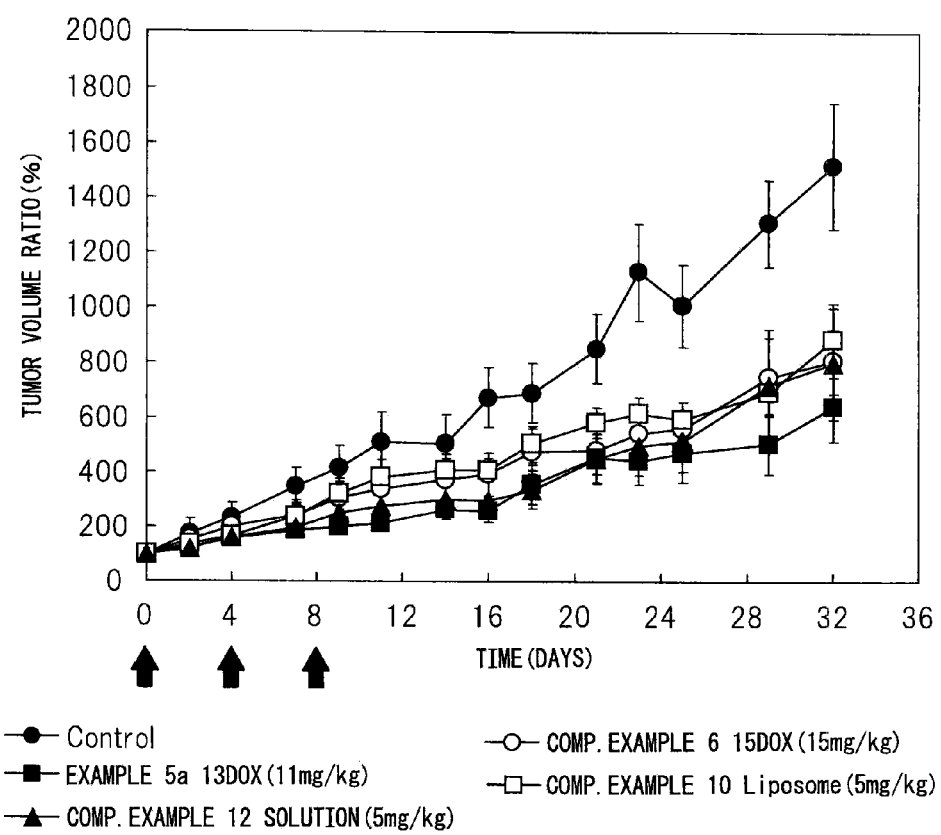

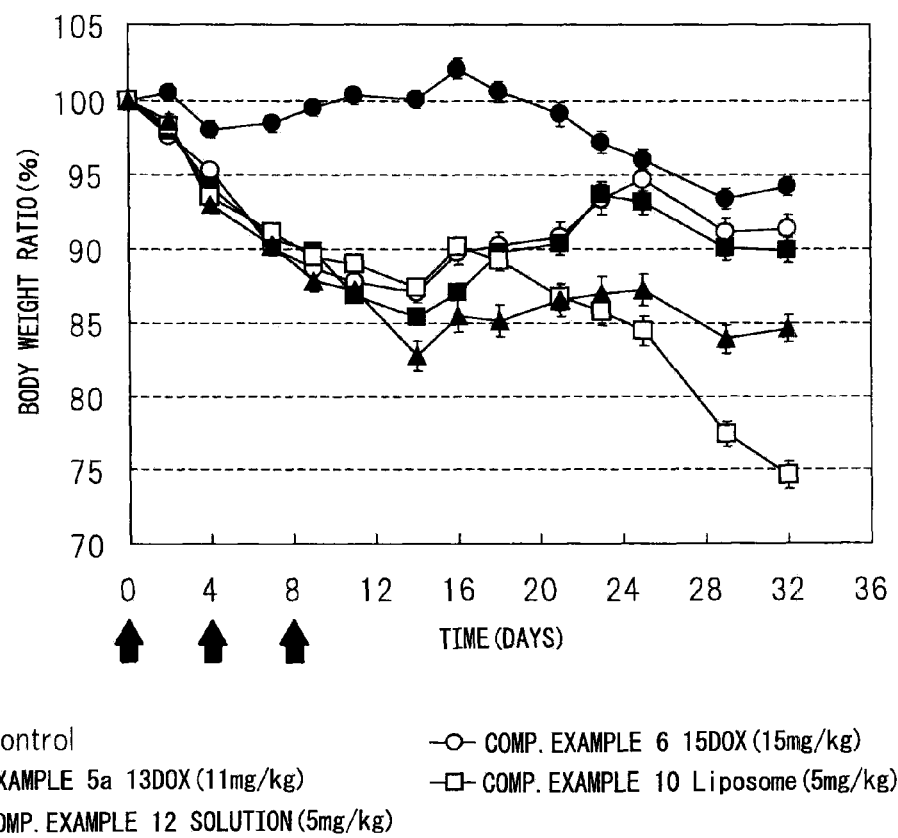

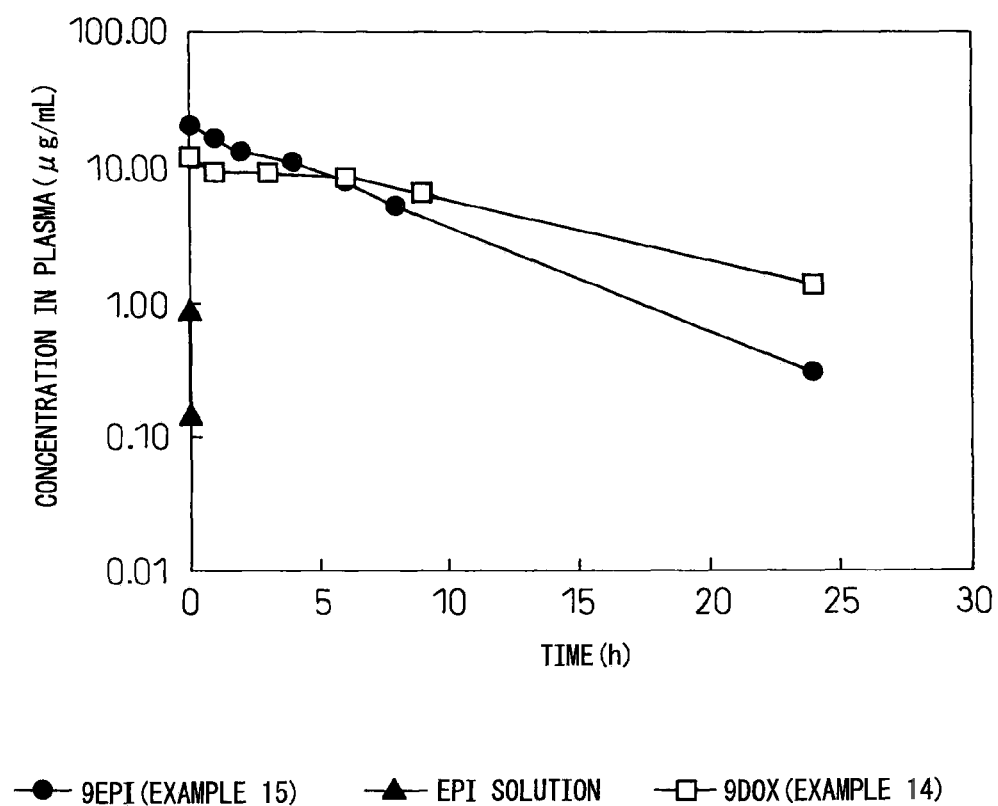

BLOCK COPOLYMER FOR DRUG CONJUGATES AND PHARMACEUTICAL COMPOSITION

TECHNICAL FIELD

The present invention provides a block copolymer for a drug conjugate that permits an excellent retention of the conjugate in the blood.

BACKGROUND ART

When a drug is systemically administered to an individual orally or by intravenous injection, etc., side effects may be recognized at normal tissues other than the focal lesions to be targeted, which may force the modification and/or suspension of the therapeutic regimen. Also for some drugs, it may be difficult to maintain the effective drug concentration, or some may be metabolized before being delivered to the target site.

In order to resolve these problems, active research is currently underway on technologies that will have introduced advanced pharmaceutical methods and concepts in which the control of the pharmacokinetics or selective delivery of a drug in the body leads to the desired drug concentration/time pattern at the action site of interest in order to optimize the therapeutic effect. These technologies and concepts are referred to as the drug delivery system (DDS), and in recent years growing importance has been recognized in that they permit the safer and more effective delivery of anti-cancer drugs, DNA, peptides etc. to pathological lesions such as tumor sites and inflammatory sites.

As specific means of DDS, a method that employs liposomes, emulsions, or nanoparticles as the drug carrier, a method in which drugs are incorporated in polymer carriers such as polymeric micelles, a method in which drugs are covalently bound to synthetic polymers or naturally occurring polysaccharides, and the like have been developed. In attempts to put these systems into practical use, there are various problems to be solved, and, among them, evasion from the biological mechanism of recognizing foreign objects, the containment of a drug at a high concentration in a DDS drug carrier, and the control of the release rate of a drug are posing serious challenges.

With regard to evasion from the biological mechanism of recognizing foreign objects, it is becoming possible to avoid the capture at the reticuloendothelial system (RES) of the liver, the spleen etc. by enhancing drug stability in the blood by coating the surface of a drug carrier such as liposomes with a hydrophilic polymer such as polyethylene glycol thereby preventing the adhesion of serum proteins, opsonin proteins etc. As a result, the high retention of liposomes and polymeric micelles in the blood circulation after intravenous administration can be obtained, and they have come to be passively accumulated in such tissues as the tumor tissues and inflammatory sites in which vascular permeability has been enhanced, thereby leading to efficient treatment.

On the other hand, with reference to the content of a drug in DDS drug carriers, a high drug content can reduce the amount of the carrier required to deliver the desired drug, which is advantageous in terms of both therapeutic effects and drug design [J. Med. Chem. 45: 4336-4343 (2002)]. Nevertheless, with regard to liposomes and polymeric micelles, the content of drugs is limited due to a poor physical stability thereof, and with regard to the polymer conjugate type, increases in drug content can affect the properties of water-soluble polymers, thereby reducing water solubility. As a result, their interaction with plasma components can no longer be controlled, retention of the conjugate in the blood circulation becomes impossible, and in most cases the drug content therein is as low as several percents [CRIPS 5(2): 2-8 (2004)]. Thus, it is impossible at present to attain a high drug content and an excellent retention in the blood at the same time.

For example, Japanese Unexamined Patent Publication (Kokai) No. 2003-34653 discloses a DDS compound which has been optimized and of which therapeutic range has been substantially expanded by a specific means for optimizing DDS, and describes that DDS compounds that make use of characteristics of each anti-cancer drug can be generated by selecting the sequence of a peptide linker for conjugating the drug and a carrier and the structure of the carrier. However, the content of anti-cancer drugs is merely about 1-10% relative to the total weight of the DDS compound.

With regard to the release of a drug, an ideal system in terms of reduced side effects and enhanced therapeutic effects is such that the drug is stably encapsulated in or bound to the carrier in the blood and, after reaching the lesional tissue, the drug is quickly released.

For example, Japanese patent No. 3270592, Japanese Unexamined Patent Publication (Kokai) No. 7-69900, and WO97/12895 disclosed pharmaceutical preparations of block copolymer-anthracycline anti-cancer drug. The drug has been encapsulated by physicochemical bonding or an amide bond utilizing the amino acid group of the drug and the carboxyl group of the block copolymer. Thus, the drug has been bound to the carrier and stabilized, but it is hardly conceivable to be quickly released after reaching the pathological tissue.

In order to highly realize the control of drug release, various environment-responsive carriers are being investigated, i.e. pharmaceutical carriers of which properties change in response to environmental changes resulting from diseases, or to differences in the environment of the normal tissue and the focal lesions.

For example, there has been reported HPMA copolymer-doxorubicin (PK1) in which doxorubicin has been bound to a HPMA polymer with a molecular weight of about 30,000 dalton via a GFLG spacer. In PK1, the drug is released by cathepsin B that is more expressed at tumor sites than at the normal tissues, and the drug content is 8.5%, i.e. it has not attained high drug content.

On the other hand, investigations are being made to attain the release of drugs in response to environmental changes due to pH changes at pathological lesions such as tumor sites and inflammatory sites by utilizing the fact that local pH at these affected regions is lower than at the normal tissues [Adv. Drug Delivery Rev. 56: 1023-1050 (2004), Biochim. Biophys. Acta. 1329(2): 291-301 (1997)].

An intracellular low-pH environment-responsive polymer conjugate [J. Controlled Release 87: 33-47 (2003)] and polymeric micelles [Bioconjugate Chem. 16: 122-130 (2005)] that release doxorubicin hydrochloride precisely in response to the low-pH environment in the endosome after the drug was incorporated into individual cancerous cells at local tumors via the endocytosis route have been reported. For this polymeric micelles, specifically, the pH dependence of drug release and a relatively high drug content have been attained.

The present inventors have found, however, that the increase in the amount of the drug in said polymeric micelles leads to reduced drug retention in the blood, and thus after intensive and extensive research, the present inventors have attained a high drug content and succeeded in enhancing retention in the blood.

DISCLOSURE OF THE INVENTION

The present invention provides a block copolymer for a drug conjugate that can resolve the above problems. The conjugate of said block copolymer and a drug permits an excellent retention in the blood compared to the nonconjugated parent compound, and therefore can expand therapeutic ranges.

The present invention comprises the following embodiments:

[1] A block copolymer for a drug conjugate, said copolymer comprising a water-soluble polymer region consisting of polyethylene glycol and a polyamino acid region having a hydrazide group and a hydrophobic group in the side chain.

[2] The block copolymer for a drug conjugate according to [1] comprising the following structure:

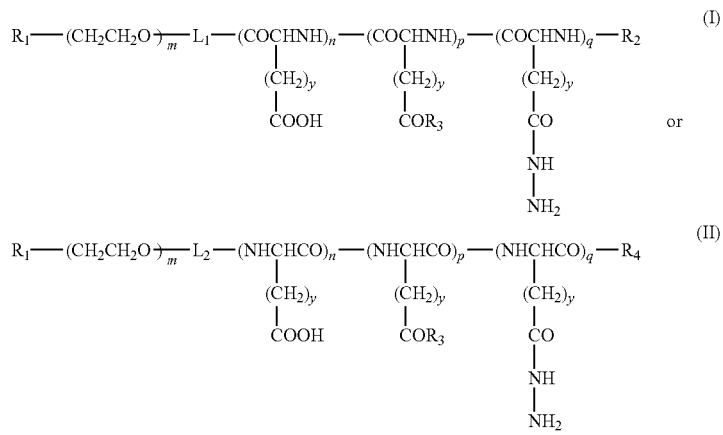

wherein $R_1$, which may be the same or different, represents a hydrogen atom, a methoxy group, a methyl group, or a substituted linear or branched or cyclic $C_1$-$C_{12}$ alkyl group, in which the substituent represents a functional group selected from the group consisting of a maleimide group, an amino group, a carboxyl group, a thiol group, a hydroxy group and an active ester group which may be protected, $R_2$ represents a hydrogen atom, a saturated or an unsaturated $C_1$-$C_{30}$ aliphatic carbonyl group or an arylcarbonyl group, $R_3$ represents —O—$R_5$ or —NH—$R_5$ in which $R_5$, which may be the same or different, represents a hydrophobic group, and $R_4$ represents a hydroxy group, a saturated or an unsaturated $C_1$-$C_{30}$ aliphatic oxy group or an aryl-lower alkyloxy group, $L_1$ and $L_2$ independently from each other represents a linker, m represents an integer of 5-1000,
n represents an integer of 0-1000,
p represents an integer of 1-1000, and
q represents an integer of 1-1000, provided that when p accounts for 20% or more to less than 90% of the total units of the polyamino acids in the block copolymer and n is present, then n, p, and q are randomly present, and when n is absent, then p and q are randomly present, and y represents an integer of 1 or 2.

[3] The block copolymer for a drug conjugate according to [2] wherein p accounts for 25% or more to 75% or less of the total units of the polyamino acids in the block copolymer.

[4] The block copolymer for a drug conjugate according to [3] wherein $R_5$ is a hydrophobic group selected from the group consisting of a benzyl group, a phenyl group, a $C_4$-phenyl group and a $C_6$-$C_{16}$ alkyl group.

[5] A drug-conjugated block copolymer wherein a drug having a ketone structure has been bound to the hydrazide group of the block copolymer for a drug conjugate according to any of [1] to [4].

[6] The drug-conjugated block copolymer according to [5] wherein the drug having a ketone structure is an anthracycline anti-cancer drug.

[7] The drug-conjugated block copolymer according to [6] wherein the anthracycline anti-cancer drug is bound at a number equal to 10% or more to 50% or less of the total units of the polyamino acids.

[8] The drug-conjugated block copolymer according to [7] wherein the anthracycline anti-cancer drug is bound at a number equal to 10% or more to 40% or less of the total units of the polyamino acids.

[9] The drug-conjugated block copolymer according to [8] wherein the anthracycline anti-cancer drug is selected from the group consisting of doxorubicin hydrochloride, daunorubicin hydrochloride, epirubicin hydrochloride, pirarubicin, idarubicin hydrochloride, amrubicin hydrochloride, nemorubicin, and PNU-159682.

[10] A polymeric micelle pharmaceutical composition comprising a water-soluble polymer region consisting of polyethylene glycol as the outer shell and an overall hydrophobic region consisting of polyamino acids and/or derivatives thereof as the inner shell, said overall hydrophobic region having a hydrazide group-bound drug and a hydrophobic group, wherein said hydrazide group-bound drug and the hydrophobic group may be present in the overall hydrophobic region in the same block copolymer, or in the overall hydrophobic region in a different block copolymer.

[11] The pharmaceutical composition according to [10] wherein the drug is bound to the hydrazide group in the block copolymer of the following formula:

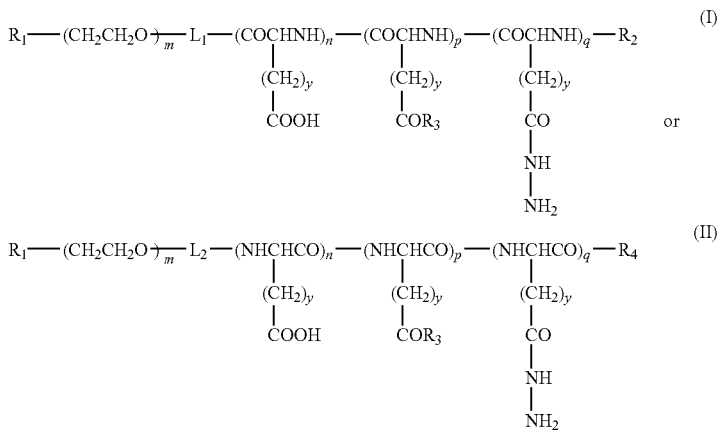

wherein
$R_1$, which may be the same or different, represents a hydrogen atom, a methoxy group, a methyl group, or a substituted linear or branched or cyclic $C_1$-$C_{12}$ alkyl group, in which the substituent represents a functional group selected from the group consisting of a maleimide group, an amino group, a carboxyl group, a thiol group, a hydroxy group and an active ester group which may be protected, $R_2$ represents a hydrogen atom, a saturated or an unsaturated $C_1$-$C_{30}$ aliphatic carbonyl group or an arylcarbonyl group, $R_3$ represents —O—$R_5$ or —NH—$R_5$ in which $R_5$, which may be the same or different, represents a hydrophobic group, $R_4$ represents a hydroxy group, a saturated or an unsaturated $C_1$-$C_{30}$ aliphatic oxy group or an aryl-lower alkyloxy group, $L_1$ and $L_2$ independently from each other represents a linker, m represents an integer of 5-1000,
n represents an integer of 0-1000,
p represents an integer of 1-1000, and
q represents an integer of 1-1000, provided that when p accounts for 20% or more to less than 90% of the total units of the polyamino acids in the block copolymer and n is present, then n, p, and q are randomly present, and when n is absent, then p and q are randomly present, and y represents an integer of 1 or 2.

[12] The pharmaceutical composition according to [11] wherein p accounts for 25% or more to 75% or less of the total units of the polyamino acids in the block copolymer.

[13] The pharmaceutical composition according to [11] wherein $R_5$ is a hydrophobic group selected from the group consisting of a benzyl group, a phenyl group, a $C_4$-phenyl group and a $C_6$-$C_{16}$ alkyl group.

[14] The pharmaceutical composition according to [11] wherein a drug having a ketone structure has been bound to the hydrazide group of the above block copolymer.

[15] The pharmaceutical composition according to [14] wherein the drug having a ketone structure is an anthracycline anti-cancer drug.

[16] The pharmaceutical composition according to [15] wherein the anthracycline anti-cancer drug is bound at a number equal to 10% or more to 50% or less of the total units of the polyamino acids.

[17] The pharmaceutical composition according to [16] wherein the anthracycline anti-cancer drug is bound at a number equal to 10% or more to 40% or less of the total units of the polyamino acids.

[18] The pharmaceutical composition according to [17] wherein the anthracycline anti-cancer drug is selected from the group consisting of doxorubicin hydrochloride, daunorubicin hydrochloride, epirubicin hydrochloride, pirarubicin, idarubicin hydrochloride, amrubicin hydrochloride, nemorubicin, and PNU-159682.

[19] The pharmaceutical composition comprising:

(1) a block copolymer wherein the drug is bound to the hydrazide group of the following formula:

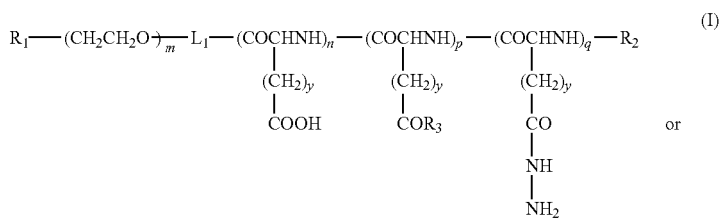

-continued

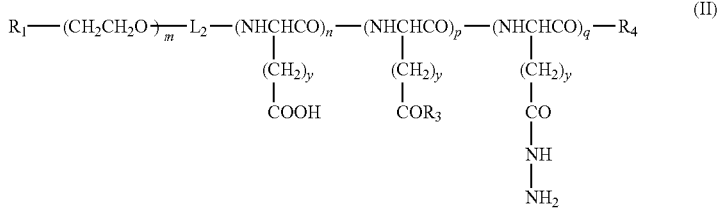

wherein

R₁, which may be the same or different, represents a hydrogen atom, a methoxy group, a methyl group, or a substituted linear or branched or cyclic $C_1$-$C_{12}$ alkyl group, in which the substituent represents a functional group selected from the group consisting of a maleimide group, an amino group, a carboxyl group, a thiol group, a hydroxy group and an active ester group which may be protected, R₂ represents a hydrogen atom, a saturated or an unsaturated $C_1$-$C_{30}$ aliphatic carbonyl group or an arylcarbonyl group, R₃ represents —O—R₅ or —NH—R₅ in which R₅, which may be the same or different, represents a hydrophobic group, and R₄ represents a hydroxy group, a saturated or an unsaturated $C_1$-$C_{30}$ aliphatic oxy group or an aryl-lower alkyloxy group, L₁ and L₂ independently from each other represents a linker, m represents an integer of 5-1000,
n represents an integer of 0-1000,
p represents an integer of 1-1000,
q represents an integer of 1-1000, and
y represents an integer of 1 or 2, and
(2) the following block copolymer:

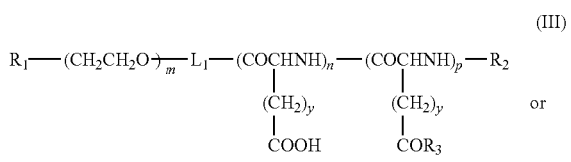

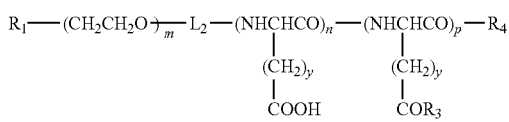

wherein

R₁, R₂, R₃, R₄, L₁, L₂, m, n, p, and y are as defined in the formulae (I) and (II), provided that when p accounts for 50% to 100% of n+p and n is present, then n and p are present randomly or in blocks.

[20] The pharmaceutical composition according to [19] wherein the drug has a ketone structure.

[21] The pharmaceutical composition according to [20] wherein the drug having a ketone structure is an anthracycline anti-cancer drug.

[22] The pharmaceutical composition according to [21] wherein the anthracycline anti-cancer drug is selected from the group consisting of doxorubicin hydrochloride, daunorubicin hydrochloride, epirubicin hydrochloride, pirarubicin, idarubicin hydrochloride, amrubicin hydrochloride, nemorubicin, and PNU-159682.

Surprisingly, it was found that by allowing the block copolymer for a drug conjugate to assume a construction comprising a water-soluble polymer region consisting of polyethylene glycol and a polyamino acid region having a hydrazide group and a hydrophobic group in the side chain, the retention of the drug in the blood circulation can markedly enhanced.

BRIEF EXPLANATION OF THE DRAWINGS

FIG. 3 shows time-courses of the total DOX concentration in the rat plasma after the intravenous administration of a DOX preparation (n=3, mean±SD).

FIG. 4 represents a release rate of the drug from the 13DOX-polymer conjugate (Example 5).

FIG. 5 represents changes with time in the tumor volume of the PC-3-xenografted nude mice after the administration of each DOX preparation (n=8, mean±SE). The arrow indicates the timing of administration.

FIG. 6 represents changes with time in the body weight of the PC-3-xenografted nude mice after the administration of each DOX preparation (n=8, mean±SE). The arrow indicates the timing of administration.

FIG. 7 shows time-courses of the total drug concentration in the plasma after the intravenous administration of a DOX-polymer conjugate (Example 14) and an EPI-polymer conjugate (Example 15) into the tail vein of male rats at 1 mg/kg in terms of the amount of the drug.

BEST MODE FOR CARRYING OUT THE INVENTION

Figure 1:
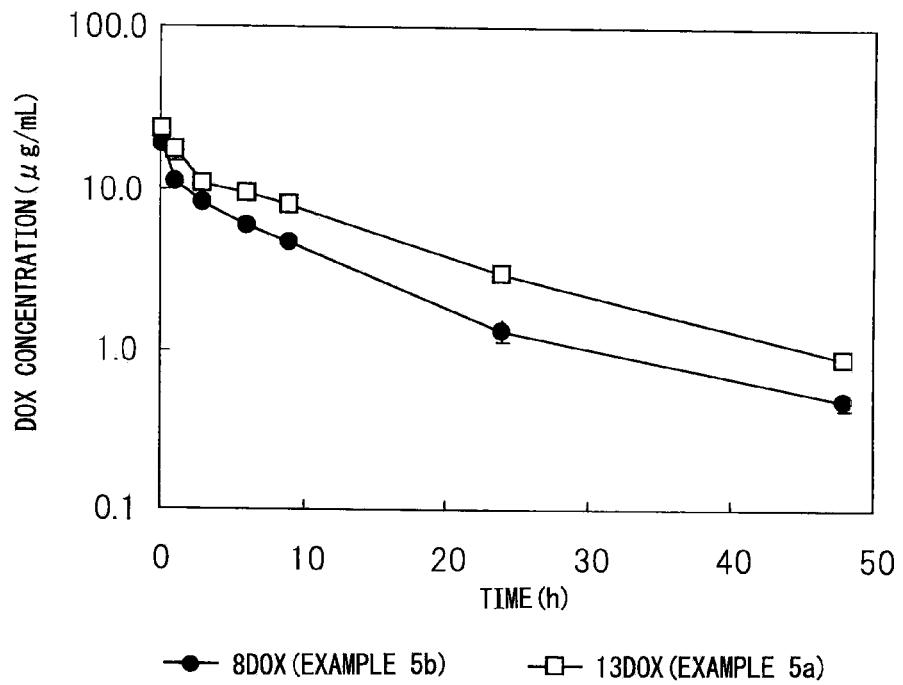
FIG. 1 shows time-courses of the total DOX concentration in the plasma after the intravenous administration of a DOX-polymer conjugate (Examples 5 and 8) into the tail vein of male rats at 1 mg/kg in terms of the amount of DOX (n=3, mean±SD).

The block copolymer for a drug conjugate of the present invention may be prepared by introducing a hydrazide group and a hydrophobic group into a block copolymer comprising a water-soluble polymer region consisting of polyethylene glycol and a polyamino acid region.

As the polyamino acid region, there can be mentioned, but not limited to, poly(amino acid derivatives) such as poly (aspartic acid) and/or a derivative thereof, poly(glutamic acid) and/or a derivative thereof, for example poly(β-alkylaspartate-co-aspartic acid), poly(β-allylaspartate-co-aspartic acid), poly(β-aralkylaspartate-co-aspartic acid), poly(γ-alkylglutamate-co-glutamic acid), poly(γ-aralkylglutamate-co-glutamic acid), poly(β-alkylaspartamide-co-aspartic acid), poly(γ-aralkylglutamide-co-glutamic acid), poly(β-benzyl-co-L-aspartate) and poly(γ-benzyl-co-L-glutamate), and the like.

Specifically, as the block copolymer that is easy to manufacture and that can be conveniently used in the present invention, those represented by the following formulae (I) and (II) may be mentioned:

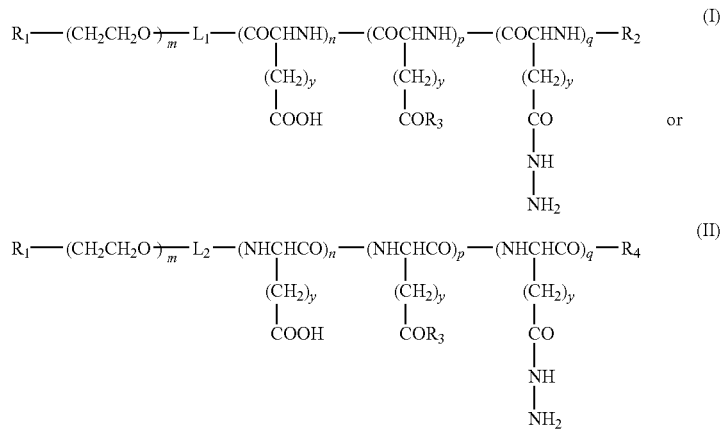

wherein $R_1$, which may be the same or different, represents a hydrogen atom, a methoxy group, a methyl group, or a substituted linear or branched or cyclic $C_1$-$C_{12}$ alkyl group, in which the substituent represents a functional group selected from the group consisting of a maleimide group, an amino group, a carboxyl group, a thiol group, a hydroxy group and an active ester group which may be protected, $R_2$ represents a hydrogen atom, a saturated or an unsaturated $C_1$-$C_{30}$ aliphatic carbonyl group or an arylcarbonyl group, $R_3$ represents —O—$R_5$ or —NH—$R_5$ in which $R_5$, which may be the same or different, represents a hydrophobic group, and $R_4$ represents a hydroxy group, a saturated or an unsaturated $C_1$-$C_{30}$ aliphatic oxy group or an aryl-lower alkyloxy group, $L_1$ and $L_2$ independently from each other represents a linker, m represents an integer of 5-1000, preferably 40-600 n represents an integer of 0-1000, preferably 0-100 p represents an integer of 1-1000, preferably 1-100, and q represents an integer of 1-1000, preferably 1-100, provided that when p accounts for 20% or more to less than 90%, preferably 25% or more to 50% or less of the total units of the polyamino acids in the block copolymer and n is present, then n, p, and q are randomly present, and when n is absent, then p and q are randomly present, and y represents an integer of 1 or 2.

The linker, which may vary depending on the method of producing the block copolymer, is not specifically limited, and $L_1$ includes, for example, —Z—NH—, —CO—Z—NH—, and —CO—NH—Z—NH— in which Z is independently a $C_1$-$C_8$ alkyl group, and $L_2$ includes, for example, —CO—Z—, —Z—CO—, —CO—Z—CO—, —Z—CO—Z—, and —Z—CO—O—Z— in which Z is independently a $C_1$-$C_8$ alkyl group.

The above block copolymer may be synthesized by reacting hydrazine or a hydrazine hydrate to a known MeO-PEG (β-benzyl-L-aspartate) thereby to convert the benzylester moiety to a hydrazide group. The reaction is usually conducted in a dehydrated solvent. Preferred solvents are aliphatic or aromatic organic solvents and those that can dissolve any of the block copolymer and hydrazine or the hydrazine hydrate. As the solvent, for example, there can be preferably used N,N-dimethylformamide, N,N-dimethylacetamide, tetrahydrofuran, dichloromethane, chloroform, or a mixed solvent thereof. The solvent used preferably doesn't contain water as much as possible.

The amount added of hydrazine during synthesis may be the amount that is desired to be introduced into the benzylester moiety of the block copolymer since the reaction proceeds in an almost quantitative manner. When hydrazine is used, for example, when 50% is to be introduced into the benzylester moiety, 0.5-fold equivalent of hydrazine is added, and when 75% is to be introduced into the benzylester moiety, 0.75-fold equivalent of hydrazine is added. The reaction is conducted at a temperature range of 0° C. to 100° C., preferably 20° C. to 80° C., and more preferably 25° C. to 50° C. The pressure is preferably normal pressure. The reaction time is not specifically limited as long as the reaction fully proceeds, and it is usually two hours to two days.

The drug that can be conjugated to the block copolymer for a drug conjugate of the present invention is not specifically limited, as long as it can form a covalent bond by reacting with a hydrazide group. Preferred examples of such a drug includes, for example, a drug that has a ketone structure, for example an anthracycline anti-cancer drug. Specific examples of anthracycline anti-cancer drugs include, for example, doxorubicin hydrochloride, daunorubicin hydrochloride, epirubicin hydrochloride, pirarubicin, idarubicin hydrochloride, amrubicin hydrochloride, nemorubicin, PNU-159682 and the like. The amount of the drug to be conjugated to said block copolymer is not specifically limited as long as retention in the blood can be maintained, and is 10% or more to 50% or less relative to the total units of polyamino acids in the block copolymer, preferably 10% or more to 40% or less, and, considering the efficacy and stability of the drug, most preferably 15% or less to 35% or less. Whereas there are plurality of ketones in the above anthracycline anti-cancer drugs, about 13 ketones bind covalently to the hydrazide group.

The binding of the above drug to the copolymer for a drug conjugate of the present invention may be preferably accomplished by simply reacting the drug to the hydrazide group of the block copolymer as much as possible under an anhydrous condition. Preferably the block copolymer of the present invention may be dissolved in a dehydrated solvent such as N,N-dimethylformamide, N,N-dimethylacetamide, tetrahydrofuran, dichloromethane, chloroform, or a mixed solvent thereof, to which the drug at the desired amount may be added and reacted at 0.1 to 10 equivalents, preferably 0.1 to 3 equivalent, relative to the hydrazide group. The reaction may be conducted at a temperature range of 0° C. to 50° C., preferably 20° C. to 40° C., and more preferably 25° C. to 37° C. The pressure is preferably normal pressure. The reaction time is not specifically limited as long as the reaction fully proceeds, and it will usually be two hours to two days. The solution after the reaction may be poured into an appropriate hydrophilic organic solvent, for example an alcohol such as 2-propanol, and the precipitate formed may be washed and collected. The collection may be performed by a centrifugation procedure. If necessary, the drug-conjugate copolymer may be subjected to purification by gel filtration chromatography or ultrafiltration to remove the unbound drug.

In another aspect, the present invention provides a polymeric micelle pharmaceutical composition comprising a water-soluble polymer region consisting of polyethylene glycol as the outer shell and an overall hydrophobic region consisting of polyamino acids and/or derivatives thereof as the inner shell, said overall hydrophobic region having a hydrazide group-bound drug and a hydrophobic group, wherein said hydrazide group-bound drug and the hydrophobic group may be present in the overall hydrophobic region in the same block copolymer or in the overall hydrophobic region in different block copolymers. As used herein the term "overall hydrophobic region" means a region that has been rendered hydrophobic due to the hydrophobic group bound to the polyamino acids and/or derivatives thereof in the block copolymer, thereby the block copolymer can form a polymeric micelle having polyethylene glycol as the outer shell in an aqueous medium at such a hydrophobic region.

The polymeric micelle in such a pharmaceutical composition may be composed of the block copolymer for a drug conjugate alone of the present invention in which the drug was conjugated to the hydrazide group (i.e. the drug conjugated to the hydrazide group and the hydrophobic group are present in the above overall hydrophobic region in the same block copolymer), or of (1) a block copolymer which comprises a water-soluble polymer region consisting of polyethylene glycol and a polyamino acid region having a hydrazide group in the side chain and optionally having a hydrophobic group, wherein the drug is conjugated to the hydrazide group, and of (2) a block copolymer which comprises a water-soluble polymer region consisting of polyethylene glycol and a polyamino acid region having a hydrophobic group and/or a derivative region thereof, wherein the drug is not conjugated to the hydrazide group.

As the block copolymer according to the above (1) in the form in which the drug is not conjugated, for example, those represented by the following formula may be used:

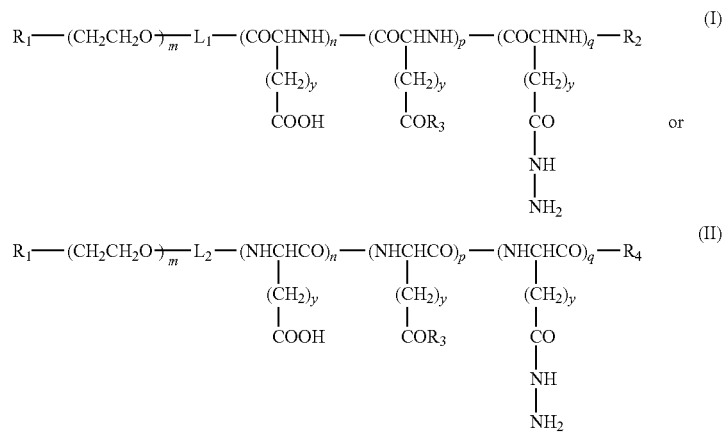

wherein
$R_1$, which may be the same or different, represents a hydrogen atom, a methoxy group, a methyl group, or a substituted linear or branched or cyclic $C_1$-$C_{12}$ alkyl group, in which the substituent represents a functional group selected from the group consisting of a maleimide group, an amino group, a carboxyl group, a thiol group, a hydroxy group and an active ester group which may be protected, $R_2$ represents a hydrogen atom, a saturated or an unsaturated $C_1$-$C_{30}$ aliphatic carbonyl group or an arylcarbonyl group, $R_3$ represents —O—$R_5$ or —NH—$R_5$ in which $R_5$, which may be the same or different, represents a hydrophobic group, and $R_4$ represents a hydroxy group, a saturated or an unsaturated $C_1$-$C_{30}$ aliphatic oxy group or an aryl-lower alkyloxy group, $L_1$ and $L_2$ independently from each other represents a linker, which may vary depending on the method of producing the block copolymer and is not specifically limited, and $L_1$ includes, for example, —Z—NH—, —CO—Z—NH—, and —CO—NH—Z—NH— in which Z is independently a $C_1$-$C_8$ alkyl group, and $L_2$ includes, for example, —Z—CO—, —CO—Z—, —CO—Z—CO—, —Z—CO—Z—, and —Z—CO—O—Z— in which Z is independently a $C_1$-$C_8$ alkyl group, m represents an integer of 5-1000, preferably 40-600
n represents an integer of 0-1000, preferably 0-100
p represents an integer of 1-1000, preferably 1-100, and
q represents an integer of 1-1000, preferably 1-100, and
y represents an integer of 1 or 2.

The introduction of a hydrazide group or the binding of a drug in the above block copolymer may be conducted pursuant to the method of producing a block copolymer for a drug conjugate of the present invention.

As the block copolymer according to the above (2), for example, those represented by the following formula may be used:

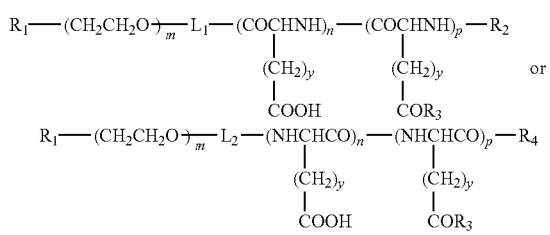

wherein $R_1$, $R_2$, $R_3$, $R_4$, $L_1$, $L_2$, m, n, p, and y are as defined in the formulae (I) and (II), provided that when n accounts for 50% to 100% of n+p and n is present, then n and p are present randomly or in blocks. The blend ratio of the block copolymer of the above (1) in which the drug was conjugated to the block copolymer and the block copolymer of the above (2) is not specifically limited, and may be mixed at a ratio in a range of 1:1 to 9:1. In this case, the percentage of the hydrophobic group to the number of the total polyamino acids in the mixed total block copolymer is 35% or more to less than 95%, preferably 50% or more to less than 95%. At this time, a hydrophobic group may be present in any copolymer of the above (1) and the above (2). The percentage of the drug that is conjugated is 5% or more to 65% or less, preferably 5% or more to 50% or less, and more preferably 5% or more to 20% or less relative to the number of the total polyamino acids in the mixed total block copolymer.

The method is not specifically limited as long as a polymeric micelle is formed, and the drug-conjugated block copolymer of the present invention may be dissolved or dispersed, and then stirred in an aqueous medium thereby to prepare polymeric micelles. At this time, physical energy such as an ultrasonic wave, pressure, shear stress or a combination thereof may be applied. The micelle may also be prepared by dissolving a block copolymer in a volatile organic solvent, followed by the evaporation of the organic solvent to dryness, then by adding an aqueous medium thereto, followed by stirring, and then by applying physical energy such as an ultrasonic wave, pressure, shear stress or a combination thereof, or by adding an aqueous medium to the block copolymer followed by applying physical energy as described above. The volatile organic solvent as used herein means methanol, ethanol, acetone, chloroform, acetonitrile, tetrahydrofuran, dichloromethane etc., and may be chosen as appropriate depending on the drug to be bound. As the aqueous medium as used herein, there can be mentioned water, physiological saline, a buffer etc., and a small amount of an organic solvent may be contained as long as it does not adversely affect the formation of polymer micelles. Considering the binding site of the drug, the pH of the buffer is preferably 6 to 8, and more preferably it is neutral.

When a drug-conjugated block copolymer and a drug-nonconjugated block copolymer are mixed to prepare a polymeric micelle, the method is not specifically limited, and, for example, after both block copolymers are dissolved in a volatile organic solvent, the organic solvent is evaporated to dryness, to which the above aqueous medium is added and stirred, and then physical energy such as an ultrasonic wave, pressure, shear stress or a combination thereof may be applied, or the aqueous medium is added to both block copolymers, to which physical energy as above may be applied to prepare the micelle. The volatile organic solvent as used herein means methanol, ethanol, acetone, chloroform, acetonitrile, tetrahydrofuran, dichloromethane etc., and may be chosen as appropriate depending on the drug to be bound.

For the polymeric micelle thus formed, the particle size is not specifically limited as long as it permits the administration to a living body, and is preferably 10 μm or less, and more preferably 5 μm or less. Specifically, when it is intravenously administered, it is preferably 200 nm or less, and more preferably 100 nm or less. If needed, the aqueous solution containing the polymeric micelle pharmaceutical composition may be filtered with a hydrophilic filter having the desired pore size. Also, a buffering agent, an isotonic agent, a stabilizing agent etc. may be added as needed to the polymeric micelle-containing pharmaceutical composition.

When a drug-conjugated block copolymer or a polymeric micelle pharmaceutical composition of the present invention is administered to a living body, the administration route is not specifically limited, and there can be mentioned intravenous, subcutaneous, intramuscular, intraarticular, intraperitoneal, intraocular administration etc. The amount administered may be chosen as appropriate depending on the type of the disease, the age, the body weight, sex etc. of the patient.

EXAMPLES

The present invention will now be explained with reference to specific examples, but they do not limit the scope of the present invention in any way.

Example 1

Synthesis of MeO-PEG-PBLA

In argon atmosphere, to 61.64 g (5.14 mmol) of polyethylene glycol having methoxy at one end and aminopropyl at the other end (MeO-PEG-NH$_2$, mean molecular weight: 12,000), 400 ml of dehydrated dimethyl sulfoxide (DMSO) and 200 ml of dehydrated N,N-dimethylformamide (DMF) were added and dissolved, to which 67.21 g (269.68 mmol) of β-benzyl-L-aspartate N-carboxylic acid anhydride (BLA-NCA, MW=249.22) was added, and allowed to react overnight at 37° C. in argon atmosphere. The solution after reaction was added dropwise to 6 L of hexane/ethyl acetate mixed solution (1/1) to precipitate a polymer. It was filtered using Kiriyama filter paper (φ 90 mm, 5B). To the polymer was added 6 liters of a clean hexane/ethyl acetate (1/1) solution, and washing with a similar procedure was repeated twice, and then it was dried under reduced pressure to obtain a powder of the methoxypolyethylene glycol-poly(β-benzyl-L-aspartate) block copolymer (MeO-PEG-PBLA). The compound obtained was confirmed to be the compound of interest by gel permeation chromatography (GPC) and $^1$H-NMR under the condition described below. From the result of GPC, the molecular weight of the polymer is Mp=20,778 Da and the molecular weight distribution of the polymer is Mw/Mn=1.06. The degree of polymerization of the polymer poly(β-benzyl-L-aspartate) (PBLA) is calculated to be 40 from the molecular weight of the PEG chain and $^1$H-NMR spectrum. The one having a molecular weight of 12,000 and a degree of polymerization of PBLA is abbreviated to be "12-40".

For convenience'sake in the Examples, the molecular weight of MeO-PEG-PBLA of 20,000 Da was used in calculation. The MeO-PEG-PBLA obtained is a block copolymer that had m=272 and n+p+1=40 as mean values in the general formula I, and in which p accounts for 100% of it.

Unless otherwise specified, the following condition was used in a similar analysis below.

[Measuring Devices and Conditions, etc.]
(1) Determination of Molecular Weight (GPC)
   System: Waters 600 GPC System
   Column: Waters Styragel HR3 (7.8φ×300 mm) (40° C.)
   Mobile phase: DMF containing 10 mM lithium chloride
   Flow rate: 0.8 ml/min
   Detection: Refractometer (RI)
(2) Nuclear Magnetic Resonance Spectrum ($^1$H-NMR)
   JEOL AL300 (300 MHz) manufactured by Nippon Denshi, solvent: DMSO-d6, temperature: room temperature.

Example 2

Synthesis of MeO-PEG-pAsp (Hyd, Bn)

In argon atmosphere, to 5 g (0.25 mmol) of MeO-PEG-PBLA (12-40) obtained in Example 1, 50 ml of dehydrated DMF was added and dissolved. Anhydrous hydrazine 159 µl (5 mmol, Mw=32.05), 0.5-fold equivalent relative to the benzylester (20 equivalents relative to the block copolymer), was added and allowed to react overnight at room temperature. After the reaction, 700 ml of 2-propanol cooled to −20° C. was added dropwise to precipitate a polymer. Centrifugation (8,000×g, 15 min, 4° C.) was carried out to collect the polymer. Washing with a similar centrifugation procedure was repeated twice with clean 2-propanol cooled to −20° C. Washing with a similar centrifugation procedure was repeated two more times with 700 ml of hexane/ethyl acetate (1/1) mixed solution. After filtration using Kiriyama filter paper (φ 45 mm, 5B), it was dried under reduced pressure to obtain a powder polymer (MeO-PEG-pAsp (Hyd, Bn)). The compound obtained was confirmed to be the compound of interest by acetylating the hydrazide group with acetic anhydride followed by $^1$H-NMR under the condition described above. From the result of $^1$H-NMR, the polyaspartic acid side chain per molecule of the polymer had 19 hydrazide groups (q), 13 benzylester groups (p), and 8 COOH (n).

Example 3

Synthesis of MeO-PEG-pAsp (Hyd, C8)

In argon atmosphere, to 1.5 g (0.075 mmol) of MeO-PEG-PBLA (12-40) obtained in Example 1, 15 ml of dehydrated DMF was added and dissolved. n-octylamine 249 µl (1.5 mmol, Mw=129.25), 0.5-fold equivalent relative to the benzylester (20 equivalents relative to the block copolymer), was added and allowed to react overnight at room temperature. Subsequently, anhydrous hydrazine 47.6 µl (1.5 mmol), 0.5-fold equivalent relative to the benzylester (20 equivalents relative to the block copolymer), was added and allowed to react overnight at room temperature.

After the reaction, it was purified in a procedure same as Example 2 to obtain a powder polymer (MeO-PEG-pAsp (Hyd, C8)). The compound obtained was confirmed to be the compound of interest by conducting acetylation as in Example 2 followed by $^1$H-NMR under the condition described above. From the result of $^1$H-NMR, the polyaspartic acid side chain per molecule of the polymer had 20 hydrazide groups (q), 11 octyl groups (p), and 9 COOH (n).

Example 4

Synthesis of MeO-PEG-pAsp (Hyd, C4-Phenyl)

In an argon atmosphere, to 1.5 g (0.075 mmol) of MeO-PEG-PBLA (12-40) obtained in Example 1, 15 ml of dehydrated DMF was added and dissolved. Anhydrous hydrazine 47.6 µl (1.5 mmol), 0.5-fold equivalent relative to the benzylester (20 equivalents relative to the block copolymer), was added and allowed to react overnight at room temperature. Then 4-phenylbutylamine 711 µl (4.5 mmol, Mw=149.23), 1.5-fold equivalent relative to the benzylester (60 equivalents relative to the block copolymer), was added and allowed to react overnight at room temperature. After the reaction, it was purified in a manner same as Example 2 to obtain a powder polymer (MeO-PEG-pAsp (Hyd, C4-Phenyl)). The compound obtained was confirmed to be the compound of interest by conducting acetylation as in Example 2 followed by $^1$H-NMR. The polyaspartic acid side chain per molecule of the polymer had 20 hydrazide groups (q), 13 phenylbutyl groups (p), and 7 COOH (n).

Example 5 a. Synthesis of MeO-PEG-pAsp (Hyd-DOX, Bn) (hereinafter, doxorubicin hydrochloride may be referred to as DOX)
   250 mg of MeO-PEG-pAsp (Hyd-DOX, Bn) obtained in Example 2 was dissolved in 0.5 ml of dehydrated DMSO, to which doxorubicin hydrochloride (DOX, Mw=580), 1.5-fold equivalent relative to the hydrazide group (30 equivalents relative to the block copolymer), was added, and was allowed to react at room temperature in the dark for 3 days. The solution after reaction was poured into 80 ml of 2-propanol cooled to −20° C. to precipitate a polymer. By centrifuging (2,380×g, 10 min, 4° C.), the polymer was collected. Washing with a similar centrifugation procedure was repeated four times with 90 ml of clean 2-propanol cooled to −20° C. Then the polymer was dissolved in 50 ml of methanol (MeOH), and purified by gel filtration chlomatograpy in a column filled with MeOH-swelled Sephadex LH-20 (manufactured by GE Healthcare Bioscience) to remove the unbound DOX. To the collected polymer solution, 8 ml of DMF was added, then concentrated by evaporation to about 30 ml, and purification with gel filtration chlomatograpy was repeated. To the collected polymer solution, 8 ml of DMF was added, and MeOH was evaporated off. Then the polypeptide solution was added dropwise to 80 ml of a hexane/ethyl acetate (1/1) mixed solution to precipitate a polymer. By a centrifugation procedure (2,380×g, 10 min, 10° C.), the polymer was collected. Then washing with a similar centrifugation procedure was repeated twice with 90 ml of clean hexane/ethyl acetate (1/1) mixed solution. After filtration using Kiriyama filter paper (φ 21 mm, 5B), it was dried under reduced pressure to obtain a powder doxorubicin hydrochloride-polymer conjugate (MeO-PEG-pAsp (Hyd-DOX, Bn)). The result of HPLC measurement described below indicated that the amount of doxorubicin hydrochloride bound per molecule of the polymer conjugate was 13, or 32.5% of the total units of the polyamino acids.

b. In a method pursuant to that described in the above a., a doxorubicin hydrochloride-polymer conjugate in which 8 molecules of doxorubicin hydrochloride bound to one molecule of the polymer was prepared.

The amount bound of doxorubicin hydrochloride in one molecule of the polymer conjugate was calculated from the measured values of HPLC of the concentrations of aspartic acid and of doxorubicin hydrochloride in the acid-hydrolyzed polymer assuming that one polymer molecule contains 40 molecules of aspartic acid. The concentration of aspartic acid was determined according to the instructions (Nihon Waters) for Waters AccQ/Tag™ amino acid analysis. On the other hand, DOX was determined by HPLC in which the DOX-polymer conjugate was dispersed in 20 mM sodium phosphate buffer (pH 7.4) to a concentration of 1 mg/ml, to a portion thereof the same amount of 0.2 N HCl was added, and allowed to stand at the final concentration of 0.1 N HCl for 1 hour at room temperature followed by HPLC determination. The condition by HPLC is as follows. Unless otherwise specified, all determinations by HPLC of DOX were conducted under the same condition.

System: Waters Alliance System
Column: Tosoh TSK-gel ODS-80™ (4.6 φ×150 mm) (40° C.)
Mobile phase: 25 mM ammonium formate (pH 3.0)/acetonitrile=7/3
Flow rate: 1 ml/min
Detection: Fluorescence (Ex: 488 nm, Em: 560 nm)
Injection volume: 10 μl Example 6

Synthesis of MeO-PEG-pAsp (Hyd-DOX, C8)

Using MeO-PEG-pAsp (Hyd, C8) obtained in Example 3, a doxorubicin hydrochloride-polymer conjugate MeO-PEG-pAsp (Hyd-DOX, C8) was obtained in the same procedure as described in Example 5. The result of HPLC determination indicated that the amount of doxorubicin hydrochloride per molecule of the polymer obtained was 12.

Example 7

Synthesis of MeO-PEG-pAsp (Hyd-DOX, C4-Phenyl)

Using MeO-PEG-pAsp (Hyd, C4-Phenyl) obtained in Example 4, a doxorubicin hydrochloride-polymer conjugate MeO-PEG-pAsp (Hyd-DOX, C4-Phenyl) was obtained in the same procedure as described in Example 5. The result of HPLC determination indicated that the amount of doxorubicin hydrochloride per molecule of the polymer obtained was 6.

Example 8

A rat PK study using MeO-PEG-pAsp (Hyd-DOX, Bn)

1) Micelle Preparation

Two compounds, i.e., the conjugate (13 DOX) obtained in Example 5a and MeO-PEG-pAsp (Hyd-DOX, Bn) (8 DOX) (Example 5b) prepared in method pursuant to Example 5a and having a different amount bound of DOX were used. An amount between 10-20 mg of each polymer was weighed accurately into a sample vial, to which 1 ml of dichloromethane was added to completely dissolve the polymer. Then, under the stream of nitrogen, the solvent was evaporated to prepare the polymer in the film form. Under reduced pressure, it was further dried at room temperature for 1 hour, and then 20 mM sodium phosphate buffer (pH 7.4)/5%(w/v) glucose was added to a polymer concentration of 10 mg/ml to hydrate the polymer film at 4° C. After stirring overnight at 4° C., it was subjected to ultrasonic treatment in ice chilled water for 10 minutes using the Biodisruptor (Nihonseiki Kaisha Ltd., High Power Unit). Subsequently, it was filtered with a 0.22 μm filter (Millipore, Millex™ GP PES) to prepare a micelle of the filtrate, which was used in the subsequent experiment.

2) Animal Study

To male Wistar rats (Charles River Laboratories Japan, Inc., 6-7 weeks old) under ether anesthesia, the above two micelles were administered into the tail vein under the following condition (n=3). Heparin-coated syringes were used to collect blood, and after centrifuging the blood drawn at 4° C., plasma was collected and stored at −30° C. until use.

Dose: 1 mg/kg in terms of the amount of DOX
Blood drawing timing: 5 minutes, 1, 3, 6, 9, 24, 48 hours after administration
Amount of blood drawn: 0.2-0.25 ml each time (from the jugular vein)

3) Determination of DOX Concentration in the Plasma a) Determination of Total DOX Concentration To 50 μl of rat plasma collected, 100 μl of acetonitrile and 50 μl of 0.4 N HCl were added in this order to make a total of 200 μl. After stirring, it was allowed to stand at room temperature for 1 hour. Subsequently, it was centrifuged (Funakoshi, Chibitan, 10,000 rpm, 10 minutes) at room temperature to collect 100 μl of the supernatant, to which 30 μl of 0.2 N NaOH, 20 μl of 1% Triton X-100, and 50 μl of 2 μg/ml of daunorubicin hydrochloride (Wako) (internal standard)/20 mM ammonium formate buffer (pH 3.0) was added in this order to make a total of 200 μl. The treatment sample liquid was filled into a HPLC sample vial, and subjected to HPLC analysis to determine the DOX concentration in the plasma.

b) Determination of Free DOX Concentration

To 50 μl of rat plasma collected, 100 μl of acetonitrile was added, centrifuged (Funakoshi, Chibitan, 10,000 rpm, 10 minutes) at room temperature to collect 50 μl of the supernatant, to which 100 μl of 2 μg/ml of daunorubicin hydrochloride (Wako) (internal standard)/20 mM sodium phosphate buffer (pH 7.4) was added. The treatment sample liquid was filled into a HPLC sample vial, and subjected to HPLC analysis to determine the DOX concentration in the plasma.

c) Calculation of a Polymer-Conjugated DOX Concentration

Using the values of the above (a) and (b), the concentration of polymer-conjugated DOX was calculated based on the following equation:

(Polymer-conjugated DOX concentration)=(total DOX concentration)−(free DOX concentration)

4) Result of Determination of Concentration Change with Time in the Plasma

Time-courses of the total DOX concentration in the plasma after intravenous administration is shown in FIG. 1. Both polymer conjugates of 8 DOX and 13 DOX showed a persistent plasma concentration, indicating an excellent retention in the blood. The concentration of free DOX was about 1/100 that of the total DOX concentration, and the DOX-polymer conjugate was stable in the blood. AUC as the total DOX concentration was 149 and 238 μg/ml·h for 8 DOX and 13 DOX, respectively. The result of AUC is shown in Table 1.

Example 9

A rat PK study using MeO-PEG-pAsp (Hyd-DOX, C8) and MeO-PEG-pAsp (Hyd-DOX, C4-Phenyl)

Using the doxorubicin hydrochloride-polymer conjugate MeO-PEG-pAsp (Hyd-DOX, C4-Phenyl) obtained in Example 7 and MeO-PEG-pAsp (Hyd-DOX, C8) obtained in Example 6, micelles were prepared similarly to Example 8, and were subjected to a rat PK study.

As a result, for MeO-PEG-pAsp (Hyd-DOX, C4-Phenyl), AUC when 1 mg/ml in terms of the amount of DOX was given into the tail vein was 156 μg/ml·h, indicating that this conjugate had an excellent retention in the blood comparable to Example 8.

For MeO-PEG-pAsp (Hyd-DOX, C8), it was 90.7 μg/ml·h, indicating this had retention in the blood superior to Comparative Example 7 described below.

Comparative Example 1

Synthesis of MeO-PEG-pAsp (Hyd)

In argon atmosphere, 6 g (0.3 mmol) of MeO-PEG-PBLA (12-40) obtained in Example 1, 60 ml of dehydrated DMF was added and dissolved. Anhydrous hydrazine 1.14 ml (36 mmol, Mw 32.05), 3-fold equivalents relative to the benzylester (120 equivalents relative to the block copolymer), was added and was allowed to react overnight at room temperature. Purification in a manner same as Example 2 gave a powder MeO-PEG-pAsp (Hyd). The compound obtained was confirmed to be the compound of interest by conducting acetylation as described in Example 2 followed by $^1$H-NMR. The polyaspartic acid side chain per molecule of the polymer had 37 hydrazide groups (q) and 3 COOH (n).

Comparative Example 2

Synthesis of MeO-PEG-pAsp (Hyd, $NH_4$)

To 2 g (0.11 mmol) of MeO-PEG-pAsp (Hyd, Bn) obtained in a manner same as Example 2, 30 ml of 0.1 N NaOH was added, and hydrolyzed at room temperature for 4 hours. Subsequently, after dialyzing against 3 liters of 0.25% ammonia solution for 2 days [molecular weight cut off (MWCO)=3,500), 0.25% ammonia solution was changed 5 times] and against 3 liters of distilled water for 2 days [molecular weight cut off (MWCO)=3,500), distilled water was changed 4 times], it was lyophilized. The polymer powder obtained was dissolved in 20 ml of DMSO, and added dropwise to 500 ml of diethyl ether to precipitate the polymer. It was filtered using Kiriyama filter paper (φ 45 mm, 5B). After repeating a similar washing twice with 400 ml of clean diethyl ether, it was dried at reduced pressure to obtain a powder MeO-PEG-pAsp (Hyd, $NH_4$). The compound obtained was confirmed to be the compound of interest by conducting acetylation as described in Example 2 followed by $^1$H-NMR. The polyaspartic acid side chain per molecule of the polymer had 18 hydrazide groups and 22 ammonium salts.

Comparative Example 3

Synthesis of MeO-PEG-pAsp (COOH)

To 2 g (0.1 mmol) of MeO-PEG-PBLA (12-40) obtained in Example 1, 16 ml (8 mmol) of 0.5 N NaOH was added, and hydrolyzed at room temperature for 2 hours. After adjusting pH to 3 with citric acid monohydrate, it was subjected to ultrafiltration (Millipore, Laboscale TFF System (UF membrane: attached to Pellicon™ XL Biomax5)) followed by filter filtration (Millipore Strivex™ GS, 0.22 μm), and then lyophilized. Subsequently, it was dissolved in 20 ml of DMF, and added dropwise to 500 ml of a hexane/ethyl acetate (1/1) mixed solution to precipitate the polymer. It was further filtered with Kiriyama filter paper (φ 45 mm, 5B). To the polymer was further added 500 ml of a clean hexane/ethyl acetate (1/1) solution, a similar procedure was repeated twice, and then it was dried under reduced pressure to obtain a powder hydrolyzate (MeO-PEG-pAsp (COOH)).

Comparative Example 4

Synthesis of MeO-PEG-pAsp (amide-DOX)

In an argon atmosphere, to 1 g (0.059 mmol) of MeO-PEG-pAsp (COOH) obtained in Comparative Example 3, 100 ml of dehydrated DMF was added and dissolved, to which doxorubicin hydrochloride 1.365 g (2.35 mmol), 1-fold equivalent relative to the carboxylic acid (40 equivalents relative to the block copolymer), dicyclohexylcarbodiimide (DCC, Mw=206.33) 728 mg (3.53 mmol), 1.5-fold equivalent relative to the carboxylic acid (60 equivalents relative to the block copolymer), and triethylamine (Mw=101.19) 492 μl (3.53 mmol), 1.5-fold equivalent relative to the carboxylic acid (60 equivalents relative to the block copolymer), were added, and allowed to react overnight at room temperature. After the reaction, the solution was dialyzed against 3 liters of water for 1 day [molecular weight cut off (MWCO)=3,500), distilled water was changed 5 times], and it was lyophilized. Then the polymer was dissolved in 20 ml of DMF, and purified by gel filtration chromatograph in a column filled with DMF-swelled Sephadex LH-20 (manufactured by GE Healthcare Bioscience). After collecting the solution, it was dialyzed against 3 liters of water for 2 days [molecular weight cut off (MWCO)=3,500), distilled water was changed 5 times], it was lyophilized. Then the polymer was dissolved in DMF, and purified by gel filtration chromatography and lyophilization were repeated to obtain the powder polymer (MeO-PEG-pAsp (amide-DOX)) wherein the amino group of DOX is bound to the carboxylic acid of the polymer via amide bonding. The result of HPLC measurement indicated that the amount bound of doxorubicin per molecule of the polymer was 13.

Comparative Example 5

Synthesis of MeO-PEG-pAsp (Hyd-DOX)

Using MeO-PEG-pAsp (Hyd) obtained in Comparative Example 1 in a procedure same as Example 5, a doxorubicin hydrochloride-polymer conjugate (MeO-PEG-pAsp (Hyd-DOX)) was obtained. The result of HPLC measurement indicated that the amount bound of doxorubicin hydrochloride per molecule of the polymer was 8.

Comparative Example 6

Synthesis of MeO-PEG-pAsp (Hyd-DOX)

Using MeO-PEG-pAsp (Hyd) obtained in Comparative Example 1 in a procedure same as Example 5, doxorubicin hydrochloride-polymer conjugates (MeO-PEG-pAsp (Hyd-DOX)) with a different amount of bound doxorubicin hydrochloride were obtained. The result of HPLC measurement indicated that the amount bound of doxorubicin hydrochloride per molecule of the polymers was 15, 20 and 39, respectively. With regard to the polymer conjugate in which 39 DOX were bound, it was thought that free DOX was also present.

Comparative Example 7

Synthesis of MeO-PEG-pAsp (Hyd-DOX, $NH_4$)

Using MeO-PEG-pAsp (Hyd, $NH_4$) obtained in Comparative Example 2 in a procedure same as Example 5, a doxorubicin hydrochloride-polymer conjugate (MeO-PEG-pAsp (Hyd-DOX, NH$_4$)) was obtained. The result of HPLC measurement indicated that the amount bound of doxorubicin hydrochloride per molecule of the polymer was 12.

Comparative Example 8

A PK study on MeO-PEG-pAsp (Hyd-DOX)

1) Preparation of Polymeric Micelles Using DOX Conjugates Obtained in Comparative Examples 5 and 6

An amount between 10-20 mg each of 4 different polymers (8, 15, 20, and 39 DOX) was weighed accurately into a sample vial, to which 1 ml of dichloromethane was added to completely dissolve the polymer. Then, under the stream of nitrogen, the solvent was evaporated to prepare the polymer in the film form. Under reduced pressure, it was further dried at room temperature for 1 hour, and then 20 mM sodium phosphate buffer (pH 7.4)/5%(w/v) glucose was added to a polymer concentration of 10 mg/ml to hydrate the polymer film at 4° C. After stirring overnight at 4° C., it was subjected to ultrasonic treatment in ice chilled water for 10 minutes using the Biodisruptor (Nihonseiki Kaisha Ltd., High Power Unit). Subsequently, it was filtered with a 0.22 μm filter (Millipore, Millex™ GP PES) to prepare polymeric micelles of the filtrate, which were used in the subsequent experiment.

2) A Rat PK Study

To male Wistar rats (Charles River Laboratories Japan, Inc., 6-7 weeks old), the above micelles were administered into the tail vein under a condition same as Example 8 (1 mg/kg as the amount of DOX, (n=3). After the collected blood was centrifuged at 4° C., DOX concentration in the plasma was determined in a method same as Example 8.

3) Result of Determination of Changes in Plasma Levels with Time

Figure 2:
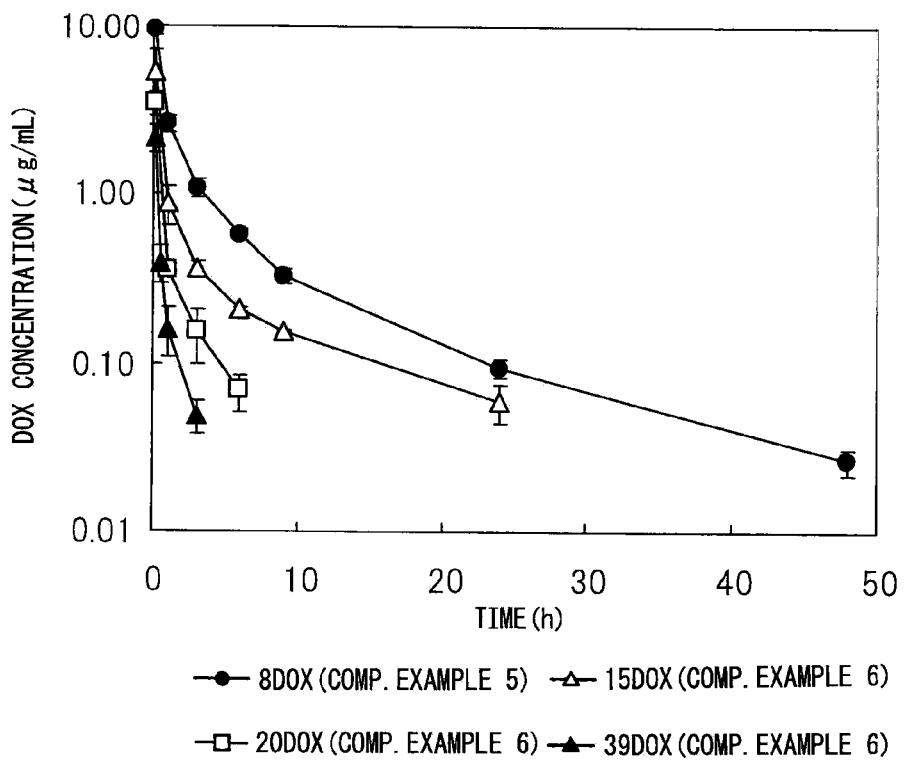
FIG. 2 shows time-courses of the total DOX concentration in the plasma after the intravenous administration of a DOX-polymer conjugate (Examples 5 and 6) into the tail vein of male Wistar rats at 1 mg/kg in terms of the amount of DOX (n=3, mean±SD).

Changes in total DOX concentration in the plasma after intravenous administration are shown in FIG. 2, and AUC calculated based on the result of this determination is summarized in Table 1. Whereas the 39 and 20 DOX-polymer conjugates rapidly disappear, the 15 and 8 DOX-polymer conjugates exhibited relatively persistent retention in the plasma. AUC of the 39, 20, 15, and 8 DOX-polymer conjugates was 1.2, 3.1, 7.6, and 19.1 μg/ml·h, respectively. However, it was 1/10 or less when compared to AUC obtained in Example 1.

Comparative Example 9

Preparation of MeO-PEG-pAsp (Amide-DOX) Micelles

An amount between 10-20 mg of the polymer MeO-PEG-pAsp (amide-DOX) obtained in Comparative Example 4 was weighed accurately into a sample vial, to which 1 ml of dichloromethane was added to completely dissolve the polymer. Then, under the stream of nitrogen, the solvent was evaporated to prepare the polymer in the film form. Under reduced pressure, it was further dried at room temperature for 1 hour, and then 20 mM sodium phosphate buffer (pH 7.4)/5% (w/v) glucose was added to a polymer concentration of 10 mg/ml to hydrate the polymer film at 4° C. After stirring overnight at 4° C., it was subjected to ultrasonic treatment in ice chilled water for 10 minutes using the Biodisruptor (Nihonseiki Kaisha Ltd., High Power Unit). Subsequently, it was gel-filtered (PD-10 column, GE Healthcare Bioscience, eluent: 20 mM sodium phosphate buffer (pH 7.4)/5% (w/v) glucose) to remove free DOX in the sample, and the collected polymer fraction was used as the polymeric micelles.

Comparative Example 10

Preparation of DOX-Encapsulating Liposomes

Using H-refined Soya lecithin (HPC) [AJINOMOTO HEALTHY SUPPLY, INC.], cholesterol (Chol) (Wako), methoxypolyethylene glycol-distearoyl phosphatidyletanoleamine carbamate conjugate (PEG-DSPE) (NOF CORPORATION, SUNBRIGHT™ DSPE-020CN, PEG chain molecular weight: 2,000), liposomes with a composition at a molar ratio of HPC:Chol:DSPE-PEG=2:1:0.1 were prepared. Thus, from the lipid chloroform stock solution, a film of the above composition was prepared under the stream of nitrogen. It was dried overnight under reduced pressure, and then 250 mM (NH$_4$)$_2$SO$_4$ aqueous solution was added thereto and hydrated at 60° C. After ulstrasonic radiation (5 minutes) at 60° C., it was subjected to a 0.1 μm filter treatment with Mini-Extruder (Avanti Polar Lipids) at 60° C. for 11 times. Subsequently, liposomes were collected by ultracentrifugation (65,000 rpm, 1 hour, 20° C., Beckman Coulter, MLA-130 rotor), and were suspended in a 5% glucose aqueous solution. To the collected empty liposomes, a DOX solution (5% (w/v) glucose) was added (lipid:DOX=1:0.2 w/w), and incubated at 65° C. for 2 hours. Subsequently, in order to remove DOX that were not encapsulated into liposomes, a similar ultracentrifugation procedure (65,000 rpm, one hour, 20° C., Beckman Coulter, MLA-130 rotor) was followed to obtain liposome as the precipitate. Furthermore, they were purified (eluent: 5%(w/v) glucose) by gel filtration (PD-10, GE Healthcare Bioscience), and the collected liposome fraction was used as a sample to be administered to rats.

Comparative Example 11

Preparation of DOX-Encapsulating Physically-Adsorbed Micelles

Synthesis of MeO-PEG-PBLA (12-40 Bn60%)

In argon atmosphere, 1 g (0.059 mmol) of MeO-PEG-pAsp (COOH) obtained in Comparative Example 3 was dissolved in 20 ml of dehydrated DMF, to which 244 μl (2.36 mmol) of benzyl alcohol, 1-fold equivalent relative to the carboxylic acid (40 equivalents relative to the block copolymer), 288 mg (2.36 mmol) of 4-dimethylamino pyridine DMAP, Mw=122.17), 1-fold equivalent relative to the carboxylic acid (40 equivalents relative to the block copolymer), and 548 μl (3.54 mmol) of diisopropyl carbodiimide (DIPCI, Mw=126.2, d: 0.815), 1.5-fold equivalent relative to the carboxylic acid (60 equivalents relative to the block copolymer), were added, and allowed to react overnight at room temperature. After the reaction the solution was added dropwise to 200 ml of a hexane/ethyl acetate (1/1) mixed solution to precipitate a polymer, which was then filtered with a Kiriyama filter paper (ϕ 45 mm, 5B). Furthermore, the polymer was washed twice with 200 ml of a clean hexane/ethyl acetate (1/1) mixed solution to obtain a polymer powder.

The polymer obtained was dispersed in 100 ml of water and then was subjected to ultrafiltration (Millipore, Laboscale TFF System (UF membrane: attached to Pellicon™ XL Biomax5)), followed by filtration (Millipore Strivex™ GS, 0.22 μm), and then lyophilized. Subsequently, it was dissolved in 20 ml of DMF, and added dropwise to 200 ml of a hexane/ethyl acetate (1/1) mixed solution to precipitate a polymer. It was further filtered with Kiriyama filter paper (φ 45 mm, 5B). Furthermore, the polymer was washed twice with 200 ml of a clean hexane/ethyl acetate (1/1) mixed solution and dried under reduced pressure to obtain a polymer powder.

The polymer obtained was confirmed under a same condition as Example 1, and the result of GPC demonstrated that the polymer had a molecular weight Mp=19500 Da and a molecular weight distribution of Mw/Mn=1.08. The introduction of benzyl groups calculated from $^1$H-NMR was 25 molecules, and the rate of introduction calculated from MeO-PEG-PBLA (12-40) obtained in Example 1 was 63%.

About 10 mg of doxorubicin hydrochloride (Wako) was accurately weighed, to which DMSO (Wako) was added to 10 mg/ml and dissolved. 2-fold moles (about 5 µl) of triethylamine (Sigma-Aldrich) relative to doxorubicin hydrochloride was added thereto, which was allowed to stand overnight at room temperature. On the other hand, as the polymer PEG-PBLA (60% Bn) (12-40) was used. About 20 mg of the polymer was accurately weighed, to which DMSO (Wako) was added and dissolved to 10 mg/ml. To the mixture, 0.4 ml of a doxorubicin hydrochloride solution in DMSO prepared above was added (polymer:DOX=1:0.2 w/w), and this mixture was placed in a dialysis membrane tube (Spectra/Por™) with a molecular weight cut off (MWCO) 3,500, and dialyzed overnight against 300 ml of 20 mM borate buffer (pH 8.0) at 4° C. The content of the dialysis membrane tube was collected, and was subjected to ultrasonication in ice chilled water for 5 minutes using the Biodisruptor (Nihonseiki Kaisha Ltd., High Power Unit). Subsequently, it was filtered with a 0.22 µm filter (Millipore, Millex™ GP PES), and then gel filtrated (PD-10 column, GE Healthcare Bioscience, eluent: 5% (w/v) glucose) to remove free DOX in the sample. The fraction collected were polymeric micelles DOX-encapsulating physically entrapped, and were used in the subsequent experiment.

Comparative Example 12

Preparation of a DOX Solution

About 10 mg of doxorubicin hydrochloride (Wako) was accurately weighed, to which a 5% (w/v) glucose aqueous solution was added to dissolve the drug completely to a concentration of 2 mg/ml, and used in the animal experiment.

Comparative Example 13

A PK Study of Comparative Examples

1) A Rat Administration Study

To male Wistar rats (Charles River Laboratories Japan, Inc., 6-7 weeks old) under ether anesthesia, the DOX preparations of the above Comparative Examples 7, and 9-12 were administered into the tail vein at 1 mg/kg (5 mg/kg for Comparative Example 12) in terms of the amount of DOX (n=3). After centrifuging the collected blood at 4° C., plasma was collected and stored at −30° C. until use.

Dose: 1 mg/kg in terms of the amount of DOX (5 mg/kg for Comparative Example 12)

Blood drawing timing: 5 minutes, 1, 3, 6, 9, 24, 48 hours after administration

Amount of blood drawn: 0.2-0.25 ml each time (from the jugular vein)

The blood collected was centrifuged at 4° C. to collect plasma, which was stored at −30° C. until use.

2) Determination of DOX Concentration

For Comparative Example 7, DOX concentration in the plasma was determined as in Example 8, and for the other Comparative Examples, the following method was used.

(1) In the Case of Liposomes

To 40 µl of rat plasma collected, 40 µl of acetonitrile was added and stirred, to which 40 µl of a 1% Triton X-100 aqueous solution was added. After centrifuging (Funakoshi, Tibitan, 10,000 rpm, 10 minutes) at room temperature, 80 µl of the supernatant was collected, to which 20 µl of 10 µg/ml of daunorubicin hydrochloride (Wako) to be used as an internal standard/25 mM ammonium formate buffer (pH 3.0) was added. The DOX concentration was determined using Waters Alliance System under the condition described in Example 8.

(2) In the Case of MeO-PEG-pAsp (Amide-DOX)

To 50 µl of rat plasma collected, 50 µl of 1N HCl was added to a total of 100 µl, and after stirring, it was warmed to 85° C. for 20 minutes. In a preliminary experiment, however, it had been confirmed that 100% of doxorubicin can be converted to related compounds. After the sample was cooled to room temperature, 100 µl of acetonitrile, 50 µl of doxorubicin hydrochloride to be used as an internal standard/1 M borate buffer (pH 8.0), and 50 µl of 1N NaOH were sequentially added and stirred. Subsequently, it was centrifuged (Funakoshi, Chibitan, 10,000 rpm, 10 minutes) at room temperature to collect 100 µl of the supernatant, which was filtered with a 0.22 µm filter (Millipore, Millex™ GP PES), and the filtrate was analyzed by HPLC. Using a calibration curve generated by treating an aqueous DOX solution in a similar manner, DOX concentration in the plasma was determined.

(3) In the Case of the DOX Solution

It was determined according to the method of determining free DOX concentration described in Example 8.

3) Result of Determination of Changes with time in Plasma Levels

The result of time-courses of the concentration of each DOX preparation in the plasma is shown in FIG. 3, and AUC calculated based on the result of this determination is summarized in Table 1. Compared to the result of the solution, an increase in AUC due to physically-entrapped polymeric micelles was 7 fold. On the other hand, in the DOX conjugate (Comparative Example 7) having an ammonium salt and a DOX-polymer conjugate (Comparative Example 9) using the amide bond, AUC increased by about 500 fold, which was however about ¼ that of Example 5. In liposome (Comparative Example 10), the increase was about 2000 fold, giving AUC almost comparable to Example 5.

TABLE 1

| AUC of each DOX preparation after intravenous administration into rats (1 mg/kg) (mean of n = 3) | |
|---|---|
| DOX preparation | AUC (µg/ml · h) |
| 8DOX (Comp. Ex. 5) | 19.1 |
| 15DOX (Comp. Ex. 6) | 7.6 |
| 20DOX (Comp. Ex. 6) | 3.1 |
| 39DOX (Comp. Ex. 6) | 1.2 |
| 12DOX (Comp. Ex. 7) | 69.5 |
| 8DOX (Example 5b) | 149 |
| 13DOX (Example 5a) | 238 |
| 6DOX (Example 7) | 156 |
| 12DOX (Example 3) | 90.7 |
| 13DOX (Amide) (Comp. Ex. 9) | 57.9 |
| DOX liposome (Comp. Ex. 10) | 267 |
| DOX physically-adsorbed micelle (Comp. Ex. 11) | 0.84 |
| DOX solution (Comp. Ex. 12) | 0.12 |

For Comparative Example 12, the dose has been corrected by diving the AUC obtained for 5 mg/kg by 5.

Example 10

Effect of the Addition of a Polymer Having a Hydrophobic Group

1) Preparation of Mixed Micelles

MeO-PEG-pAsp (Hyd-DOX) (Comparative Example 6) containing 39 molecules of DOX in one polymer was used. An amount between 10-20 mg each of this conjugate and PEG-PBLA (60% Bn) (12-40) having a hydrophobic group prepared in Comparative Example 11 was accurately weighed into a sample vial so as to give a weight ratio of 1:1, and then 1 ml of dichloromethane was added thereto to dissolve the polymer completely. Subsequently, under the stream of nitrogen, the solvent was evaporated to prepare a polymer in the film form. After it was further dried under reduced pressure at room temperature for 1 hour, 20 mM sodium phosphate buffer (pH 7.4)/5% (w/v) glucose was added to a polymer concentration of 10 mg/ml to hydrate the polymer film at 4° C. After stirring overnight at 4° C., it was subjected to ultrasonic treatment in ice chilled water for 10 minutes using the Biodisruptor (Nihonseiki Kaisha Ltd., High Power Unit). Subsequently, it was filtered with a 0.22 μm filter (Millipore, Millex™ GP PES) to prepare micelles of the filtrate, which were used in the subsequent experiment.

2) A Rat PK Study and the Result

In a method same as Example 8, the above micelles were intravenously administered to a dose of 1 mg/kg in terms of the amount of DOX. By determining changes in the concentration in the plasma, AUC was calculated to be 12.4 μg/ml·h, indicating an improvement of AUC by about 10-fold as compared to when the DOX-polymer conjugate was only used in preparation (described in Comparative Example 13). The result demonstrates that by adding a block copolymer having a hydrophobic group, the stability of DOX-polymer conjugate micelles in the blood can be enhanced.

Example 11

A Study on pH-Dependency of Drug Release

About 10 mg of the polymer obtained in Example 5 was weighed accurately into a sample vial, to which 1 ml of dichloromethane was added to completely dissolve the polymer. Then, under the stream of nitrogen, the solvent was evaporated to prepare the polymer in the film form. Under reduced pressure, it was further dried at room temperature for 1 hour, and then 20 mM sodium phosphate buffer (pH 7.4) was added to a polymer concentration of 10 mg/ml to hydrate the polymer film at 4° C. After stirring overnight at 4° C., it was subjected to ultrasonic treatment in ice chilled water for 10 minutes using the Biodisruptor (Nihonseiki Kaisha Ltd., High Power Unit). Subsequently, it was filtered with a 0.22 μm filter (Millipore, Millex™ GP PES) to prepare micelles of the filtrate, which were used in the subsequent experiment.

To 950 μl of 20 mM ammonium formate buffer (pH 3), sodium acetate buffer (pH 5), or sodium phosphate buffer (pH 7.4) previously heated to 37° C., 50 μl of the polymeric micelles prepared in the above method were added to initiate a drug release experiment. At predetermined timing, 50 μl of the sample was collected, and instead the liquid amount was replenished with the same buffer, The free DOX concentration in the collected sample was determined by HPLC according to the above-mentioned method.

The result is shown in FIG. 4. While DOX was rapidly released at pH 3, the release rate decreased as the pH of the liquid becomes neutral to pH 5 to 7.4, thereby confirming the pH dependency.

Example 12

A Drug Efficacy Study

Human prostate cancer PC-3 cells subcutaneous transplanted to male nude mice were used as the model for evaluating drug efficacy.

Male nude mice (Balb nu/nu, 5 weeks old) were purchased from Charles River Laboratories Japan, Inc., and human prostate cancer PC-3 cells were purchased from the Human Health Sciences Foundation Resources Bank. PC-3 cells that had been subcultured in a $CO_2$ incubator were suspended in physiological saline for injection (Otsuka Pharmaceutical Co., Ltd.), and were subcutaneously injected into the back of the nude mice to a cell count of $2\times10^6$/50 μl per animal. Then, after keeping the nude mice for about 2 weeks, the administration of the drug was started when the mean of tumor volume reached about 50 $mm^3$. The DOX-polymer conjugates (two regimens: Example 5 and Comparative Example 6) were administered into the tail vein (every 4 days for a total of 3 times), and anti-tumor effect was assessed from tumor volume, and side effects from changes in body weight (8 animals per group). For comparison, the DOX solution (Comparative Example 12) and the DOX-encapsulating liposomes (Comparative Example 10) were used. The amount administered of each preparation was MTD (Comparative Examples 6, 10, 12) previously determined using normal healthy mice or ⅔ the amount (Example 5).

Changes in tumor volume and body weight are shown in FIG. 5 and FIG. 6. In the case of the DOX solution (Comparative Example 12), the body weight decreased by a maximum of 17% at the MTD of 5 mg/kg and the effect of inhibiting tumor growth was T/C=0.4 at the maximum [T/C: the ratio of tumor volume of the drug administration group (T) to that of the control group (C)]. In the case of liposomes (Comparative Example 10), a reduction in body weight of 20% or more at the MTD of 5 mg/kg persisted to the end of the experiment, and inhibited tumor growth up to T/C=0.43. In the case of the DOX-polymer conjugate (Comparative Example 6), body weight decreased by a maximum of 13% at 15 mg/kg, and inhibited tumor up to T/C=0.42. In Example 5, body weight reduced a maximum of 15% at MTD×⅔ of 11 mg/kg, whereas it switched and started to increase on day 16 post-administration and after, and exhibited the effect of inhibiting tumor growth up to T/C=0.32. The foregoing result indicates that the DOX-polymer conjugate (Example 5) has an excellent anti-tumor effect as compared to the DOX solution or the DOX-encapsulating liposomes.

Example 13

Synthesis of MeO-PEG-pAsp (Hyd, Bn)

Except that the equivalent ratio of anhydrous hydrazine was changed, the polymer was synthesized based on the synthetic method described in Example 2. Specifically, 79.3 μl (2.5 mmol, Mw=32.05) of anhydrous hydrazine, 0.25-fold equivalent relative to the benzylester (10 equivalents relative to the block copolymer) in 5 g (0.25 mmol) of MeO-PEG-PBLA (12-40) was added to obtain a powder polymer (MeO-PEG-pAsp (Hyd, Bn)). The compound obtained was confirmed to be the compound of interest by conducting acetylation of the hydrazide group same as to Example 2, followed by $^1$H-NMR. The polyaspartic acid side chain per molecule of the polymer had 10 hydrazide groups (q), 26 benzylester groups (p), and 4 COOH (n).

Example 14

Synthesis of MeO-PEG-pAsp (Hyd-DOX, Bn)

500 mg of MeO-PEG-pAsp (Hyd, Bn) obtained in Example 13 was dissolved in 5 ml of dehydrated DMSO, to which 2-fold equivalents of doxorubicin hydrochloride (DOX, MW=580) relative to the hydrazide group (20 equivalents relative to the block copolymer) was added, and was allowed to react at 37° C., in the dark for 3 days. After the reaction, it was purified in a same manner as Example 5 to obtain a doxorubicin hydrochloride-polymer conjugate (MeO-PEG-pAsp (Hyd-DOX, Bn)). The result of HPLC indicated that the amount of doxorubicin hydrochloride per molecule of the polymer conjugate was 9.

Example 15

Synthesis of MeO-PEG-pAsp (Hyd-EPI, Bn)

Except that doxorubicin hydrochloride was replaced with epirubicin hydrochloride, a method similar to that of Example 14 was followed in which 2-fold equivalents of epirubicin hydrochloride (hereinafter referred to as EPI, MW=580) relative to the hydrazide group (20 equivalents relative to the block copolymer) was added, and was allowed to react for 3 days to obtain a epirubicin hydrochloride-polymer conjugate (MeO-PEG-pAsp (Hyd-EPI, Bn)). The result of determination by HPLC indicated that the amount of epirubicin hydrochloride per molecule of the polymer conjugate obtained was 9.

Example 16

A Rat PK Study Using MeO-PEG-pAsp (Hyd-DOX, Bn) and MeO-PEG-pAsp (Hyd-EPI, Bn)

Using the doxorubicin hydrochloride-polymer conjugate (MeO-PEG-pAsp (Hyd-DOX, Bn)) obtained in Example 14 and the epirubicin hydrochloride-polymer conjugate (MeO-PEG-pAsp (Hyd-EPI, Bn)) obtained in Example 15, micelles were prepared same as Example 8, and were subjected to a rat PK study. The measurement of EPI concentration in the plasma was carried out same as the measurement of DOX concentration described in Example 8.

As a result, for MeO-PEG-pAsp (Hyd-DOX, Bn), AUC, when 1 mg/ml in terms of the amount of DOX was given into the tail vein, was 142 μg/ml·h, indicating that this conjugate had an excellent retention in the blood comparable to Example 8. For MeO-PEG-pAsp (Hyd-EPI, Bn) as well, AUC, when 1 mg/ml in terms of the amount of EPI was given into the tail vein, was 132 μg/ml·h, also indicating that this also had excellent retention in the blood.

On the other hand, when about 10 mg of epirubicin hydrochloride (Shandong Newtime Pharmaceuticals) was accurately weighed, to which a 5% (w/v) glucose aqueous solution was added and dissolved completely, and 1 mg/kg of it was administered into the tail vein, AUC was 0.04 μg/ml·h.

These time-courses of drug concentration in the plasma after intravenous administration are shown in FIG. 7. As compared to the epirubicin hydrochloride solution, either polymer conjugate of DOX and EPI exhibited persistent plasma concentration indicating that they had excellent retention in the blood compared to the Comparative Examples.

The foregoing description of the present invention is for the purpose of illustration and explanation. It should be noted that various modifications may be possible without departing from the spirit and scope of the present invention. Thus, the claim intends to encompass all such modifications.

The invention claimed is:

1. A drug conjugated block copolymer in which a drug having a ketone structure being bound to a hydrazide group of the block copolymer, said block copolymer comprising a water-soluble polymer region consisting of polyethylene glycol and a polyamino acid region having a hydrazide group and a hydrophobic group in the side chain, wherein the block copolymer comprises the following structure:

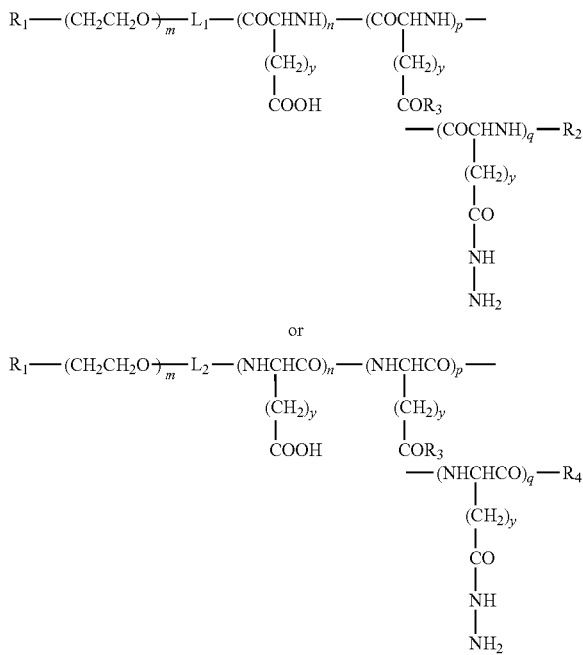

wherein $R_1$, which may be the same or different, represents a hydrogen atom, a methoxy group, a methyl group, or a substituted linear or branched or cyclic $C_1$-$C_{12}$ alkyl group, in which the substituent represents a functional group selected from the group consisting of a maleimide group, an amino group, a carboxyl group, a thiol group, a hydroxy group and an active ester group which may be protected, $R_2$ represents a hydrogen atom, a saturated or an unsaturated $C_1$-$C_{30}$ aliphatic carbonyl group or an arylcarbonyl group, $R_3$ represents —O—$R_5$ or —NH—$R_5$ in which $R_5$, which may be the same or different, represents a hydrophobic group, and $R_4$ represents a hydroxy group, a saturated or an unsaturated $C_1$-$C_{30}$ aliphatic oxy group or an aryl-lower alkyloxy group, $L_1$ and $L_2$ independently from each other represents a linker, m represents an integer of 5-1000, n represents an integer of 0-1000, p represents an integer of 1-1000, and q represents an integer of 1-1000, provided that when units having a hydrophobic group in the side chain account for 25% or more 75% or less of the total units of the polyamino acids in the block copolymer and when units having a carboxylic acid group in the side chain are present, then the units having a carboxylic acid group in the side chain, units having a hydrophobic group in the side chain, and units having a hydrazide group in the side chain are randomly distributed throughout the polyamino acid region, and when units having a carboxylic acid group in the side chain are absent, then the units having a hydrophobic group in the side chain and units having a hydrazide group in the side chain are randomly distributed throughout the polyamino acid region, and y represents an integer of 1 or 2, and wherein as a result of said drug being bound to said block copolymer, the units having a hydrazide group in the side chain account for more than 0% to 35% or less of the total units of the polyamino acids in the block copolymer.

2. The drug-conjugated block copolymer according to claim 1 wherein $R_5$ is a hydrophobic group selected from the group consisting of a benzyl group, a phenyl group, a $C_4$-phenyl group and a $C_6$-$C_{16}$ alkyl group.

3. The drug-conjugated block copolymer according to claim 1 wherein the drug having a ketone structure is an anthracycline anti-cancer drug.

4. The drugs-conjugated block copolymer according to claim 3 wherein the anthracycline anti-cancer drug is bound at a number equal to 10% or more to 35% or less of the total units of the polyamino acids.

5. The drug-conjugated block copolymer according to claim 4 wherein the anthracycline anti-cancer drug is selected from the group consisting of doxorubicin hydrochloride, daunorubicin hydrochloride, epirubicin hydrochloride, pirarubicin, idarubicin hydrochloride, amrubicin hydrochloride, nemorubicin, and PNU-159682.

6. A polymeric micelle pharmaceutical composition formed by the drug-conjugated block copolymer according to claim 1 comprising a water-soluble polymer region consisting of said polyethylene glycol as the outer shell and an overall hydrophobic region consisting of said polyamino acids as the inner shell, said overall hydrophobic region having said hydrazide group-bound drug and said hydrophobic group, wherein said hydrazide group-bound drug and the hydrophobic group may be present in the overall hydrophobic region in the same block copolymer, or in the overall hydrophobic region in a different block copolymer.

* * * * *

UNITED STATES PATENT AND TRADEMARK OFFICE
CERTIFICATE OF CORRECTION

PATENT NO. : 8,519,051 B2  Page 1 of 1
APPLICATION NO. : 12/445710
DATED : August 27, 2013
INVENTOR(S) : Bobe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Fifteenth Day of September, 2015

Michelle K. Lee
*Director of the United States Patent and Trademark Office*